US008227636B2

(12) United States Patent
Miller et al.

(10) Patent No.: US 8,227,636 B2
(45) Date of Patent: Jul. 24, 2012

(54) HISTONE DEACETYLASE INHIBITOR PRODRUGS

(75) Inventors: Thomas A. Miller, New York, NY (US); David J. Witter, Putnam Valley, NY (US); Sandro Belvedere, New York, NY (US)

(73) Assignee: Merck HDAC Research, LLC, Boston, MA (US)

( * ) Notice: Subject to any disclaimer, the term of this patent is extended or adjusted under 35 U.S.C. 154(b) by 1167 days.

(21) Appl. No.: 10/594,483

(22) PCT Filed: Apr. 5, 2005

(86) PCT No.: PCT/US2005/011463
§ 371 (c)(1),
(2), (4) Date: Mar. 3, 2008

(87) PCT Pub. No.: WO2005/097747
PCT Pub. Date: Oct. 20, 2005

(65) Prior Publication Data
US 2009/0023786 A1 Jan. 22, 2009

Related U.S. Application Data

(60) Provisional application No. 60/559,715, filed on Apr. 5, 2004.

(51) Int. Cl.
C07C 69/02 (2006.01)
A61K 31/22 (2006.01)
(52) U.S. Cl. ............ 560/129; 549/57; 549/72; 546/318; 514/356; 514/443; 514/448; 514/478; 514/507; 514/546; 560/32; 560/312
(58) Field of Classification Search .................... 560/32, 560/129, 312; 514/478, 448, 443, 356, 507, 514/546; 546/318; 549/57, 72
See application file for complete search history.

(56) References Cited

U.S. PATENT DOCUMENTS

| 3,465,024 | A | * | 9/1969 | Brownstein et al. | 560/338 |
| 3,577,458 | A | * | 5/1971 | Brownstein et al. | 562/874 |
| 4,522,811 | A | | 6/1985 | Eppstein et al. | 514/2 |
| 5,369,108 | A | | 11/1994 | Breslow et al. | 514/266 |
| 5,608,108 | A | | 3/1997 | Marks et al. | 562/621 |
| 5,700,811 | A | | 12/1997 | Breslow et al. | 514/314 |
| 5,932,616 | A | | 8/1999 | Breslow et al. | 514/532 |
| 6,087,367 | A | | 7/2000 | Breslow et al. | 514/266 |
| 6,511,990 | B1 | | 1/2003 | Breslow et al. | 514/314 |
| 6,713,646 | B2 | * | 3/2004 | Zhang et al. | 560/205 |
| 7,126,001 | B2 | | 10/2006 | Breslow et al. | 546/171 |
| 2003/0235588 | A1 | | 12/2003 | Richon et al. | 514/575 |
| 2004/0087657 | A1 | | 5/2004 | Richon et al. | 514/575 |
| 2004/0266818 | A1 | | 12/2004 | Breslow et al. | 514/310 |

FOREIGN PATENT DOCUMENTS

| JP | 2002-128769 | 5/2002 |
| WO | WO93/02037 | 2/1993 |
| WO | WO 97/11366 | 3/1997 |
| WO | WO 98/48825 | 11/1998 |
| WO | WO 00/08048 | 2/2000 |
| WO | WO 2005/348800 | 4/2005 |
| WO | WO 2005/053610 | 6/2005 |
| WO | WO 2005/097747 | 10/2005 |

OTHER PUBLICATIONS

West, Anthony R., Solid State Chemistry and its Applications, Wiley, New York, 1988, pp. 358 & 365.*
Hurd et al, J. Org. Chem., 1946, 11, 207-14(abstract only).*
Carter et al., Chemotherapy of Cancer, second edition, John Wiley & Sons, N.Y., N.Y., 1981, pp. 362-365.*
Abe, E., et al., Proc. Natl. Acad. Sci. (USA) 78:4990-4994 (1981).
Andrews et al., International J. Parasitology 30,761-768 (2000).
Archer, S. et al., PNAS 95:6791-96 (1998).
Berge, et al., J. Pharm. Sci., 66:1-19 (1977).
Brosch et al., Plant Cell 7, 1941-1950 (1995).
Butler, L.M. et al., Cancer Res. 60:5165-5170 (2000).
Cohen, L.A. et al., Anticancer Research 19:4999-5006 (1999).
Cousens et al., J. Biol. Chem. 254,1716-1723 (1979).
Darkin-Rattray et al., Proc. Natl. Acad. Sci. USA 93,13143-13147 (1996).
Dressel, U. et al., Anticancer Research 20(2A):1017-22 (2000).
Ebert, P. S., et al. Cancer Res. 36: 1809-1813 (1976).
Finnin, M.S., et al., Nature 401:188-193 (1999).
Frey et al, Bioorganic & Med. Chem. Lett., 12, 3443-3447 (2002).
Friend, C., et al., Proc. Natl. Acad. Sci., U. S., 68:378-382 (1971).
Grunstein, M., Nature, 389: 349-52 (1997).
Guan et al., Cancer Research, 60,749-755 (2000).
Hayashi, M., et al., Gann 70: 235-238 (1979).
Huberman, E. et al., Proc. Natl. Acad. Sci. (USA) 76: 1293-1297 (1979).
Kijima et al., J Biol. Chem. 268,22429-22435 (1993).
Kim et al., Oncogene, 18: 2461-2470 (1999).
Koghe et al., Biochem. Pharmacol. 56: 1359-1364 (1998).
Kwon et al., PNAS 95: 3356-3361 (1998).
Lea et al., Anticancer Research, 15, 879-873 (1995).
Lin, R.J. et al., Nature 391:811-14 (1998).
Lotem, J., et al., Int. J. Cancer 15: 731-740 (1975).
Lotem, J. et al., Proc. Natl. Acad. Sci. (USA) 76: 5158-5162 (1979).

(Continued)

Primary Examiner — Shailendra Kumar
(74) Attorney, Agent, or Firm — Li Su; David A. Muthard

(57) ABSTRACT

The present invention is directed to prodrugs of hydroxamic acid based histone deacetylase (HDAC) inhibitors, e.g., suberoylanilide hydroxamic acid (SAHA). The prodrugs are acylated derivatives having increased aqueous solubility and cellular permeability as compared with the free hydroxamic acid, and are useful for inhibiting HDACs, and for selectively inducing terminal differentiation, cell growth arrest and/or apoptosis of neoplastic cells, thereby inhibiting proliferation of such cells. Thus, the prodrugs of the present invention are useful in treating a patient having a tumor characterized by proliferation of neoplastic cells. The prodrugs of the invention are also useful in the prevention and treatment of thioredoxin (TRX)-mediated diseases, such as autoimmune, allergic and inflammatory diseases, and in the prevention and/or treatment of diseases of the central nervous system (CNS), such as neurodegenerative diseases.

30 Claims, No Drawings

OTHER PUBLICATIONS

Marks, P. et al., Cancer Res. 47:659 (1987).
Marks, P.A. et al., J. Natl. Cancer Inst., 92:1210-1215 (2000).
McBain et al., Biochem. Pharm. 53: 1357-1368 (1997).
Metcalf, D., et al., Science, 229: 16-22 (1985).
Morin, M. J., et al., Cancer Res. 44: 2807-2812 (1984).
Nakajima et al., Ex. Cell Res. 241,126-133 (1998).
Qiu et al., Mol. Biol. Cell 11, 2069-2083 (2000).
Reuben, R. C., et al., Proc. Natl. Acad. Sci. (USA) 73: 862-866 (1976).
Richon et al., Proc. Natl. Acad. Sci. USA, 93:5705-5708 (1996).
Richon, V. M. et al., Proc. Natl. Acad. Sci., USA, 95:3003-3007 (1998).
Sachs, L., Nature (Lond.) 274: 535 (1978).
Saito et al., Proc. Natl. Acad. Sci. USA 96, 4592-4597 (1999).
Scher, W. et al., Exp. Hematol. 11: 490-498 (1983).
Scher, W., et al., Biochem. & Biophys. Res. Comm. 109: 348-354) (1982).
Schwartz, E. L. et al., Cancer Res. 42: 2651-2655 (1982).
Schwartz, E. L., et al., Cancer Res. 43: 2725-2730 (1983).
Schwartz, E. L., et al., Proc. Am. Assoc. Cancer Res. 24: 18 (1983).
Su et al., Cancer Research, 60: 3137-3142 (2000).
Sugano, H., et al., Bibl. Hematol. 39: 943-954 (1973).
Takenaga, K., et al., Cancer Res. 40: 914-919 (1980).
Tanaka, M., et al., Proc. Natl. Acad. Sci. (USA) 72: 1003-1006 (1975).
Terada, M., et al., Proc. Natl. Acad. Sci. (USA) 75: 2795-2799 (1978).
Van Lint, C. et al., *Gene Expression* 5:245-53 (1996).
Wang et al., Cancer Research 59, 2766-2799 (1999).
Yoshida, M. et al., J. Biol. Chem. 265:17174-17179, (1990).
International Search Report for PCT/US05/011463 mailed Jul. 26, 2005.

* cited by examiner

HISTONE DEACETYLASE INHIBITOR PRODRUGS

This application is a 371 of PCT/US05/11463, filed Apr. 5, 2005, which claims benefit of 60/559,715, filed Apr. 5, 2004.

FIELD OF THE INVENTION

The present invention is directed to prodrugs of hydroxamic acid based histone deacetylase (HDAC) inhibitors, e.g., suberoylanilide hydroxamic acid (SAHA). The prodrugs are acylated derivatives having increased aqueous solubility and cellular permeability as compared with the free hydroxamic acid, and are useful for inhibiting HDACs, and for selectively inducing terminal differentiation, cell growth arrest and/or apoptosis of neoplastic cells, thereby inhibiting proliferation of such cells. Thus, the prodrugs of the present invention are useful in treating a patient having a tumor characterized by proliferation of neoplastic cells. The prodrugs of the invention are also useful in the prevention and treatment of thioredoxin (TRX)-mediated diseases, such as autoimmune, allergic, and inflammatory diseases, and in the prevention and/or treatment of diseases of the central nervous system (CNS), such as neurodegenerative diseases.

BACKGROUND OF THE INVENTION

Compounds having a hydroxamic acid moiety have been shown to possess useful biological activities. For example, many peptidyl compounds possessing a hydroxamic acid moiety are known to inhibit matrix metalloproteinases (MMPs), which are a family of zinc endopeptidases. The MMPs play a key role in both physiological and pathological tissue degradation. Therefore, peptidyl compounds that have the ability to inhibit the action of MMPs show utility for the treatment or prophylaxis of conditions involving tissue breakdown and inflammation. Further, compounds having a hydroxamic acid moiety have been shown to inhibit histone deacetylases (HDACs), based at least in part on the zinc binding property of the hydroxamic acid group.

The inhibition of HDACs can repress gene expression, including expression of genes related to tumor suppression. Inhibition of histone deacetylase can lead to the histone deacetylase-mediated transcriptional repression of tumor suppressor genes. For example, inhibition of histone deacetylase can provide a method for treating cancer, hematological disorders, such as hematopoiesis, and genetic related metabolic disorders. More specifically, transcriptional regulation is a major event in cell differentiation, proliferation, and apoptosis. There are several lines of evidence that histone acetylation and deacetylation are mechanisms by which transcriptional regulation in a cell is achieved (Grunstein, M., Nature, 389: 349-52 (1997)). These effects are thought to occur through changes in the structure of chromatin by altering the affinity of histone proteins for coiled DNA in the nucleosome. There are five types of histones that have been identified. Histones H2A, H2B, H3, and H4 are found in the nucleosome and H1 is a linker located between nucleosomes. Each nucleosome contains two of each histone type within its core, except for H1, which is present singly in the outer portion of the nucleosome structure. It is believed that when the histone proteins are hypoacetylated, there is a greater affinity of the histone to the DNA phosphate backbone. This affinity causes DNA to be tightly bound to the histone and renders the DNA inaccessible to transcriptional regulatory elements and machinery.

The regulation of acetylated states occurs through the balance of activity between two enzyme complexes, histone acetyl transferase (HAT) and histone deacetylase (HDAC). The hypoacetylated state is thought to inhibit transcription of associated DNA. This hypoacetylated state is catalyzed by large multiprotein complexes that include HDAC enzymes. In particular, HDACs have been shown to catalyze the removal of acetyl groups from the chromatin core histones.

It has been shown in several instances that the disruption of HAT or HDAC activity is implicated in the development of a malignant phenotype. For instance, in acute promyelocytic leukemia, the oncoprotein produced by the fusion of PML and RAR alpha appears to suppress specific gene transcription through the recruitment of HDACs (Lin, R. J. et al., Nature 391:811-14 (1998)). In this manner, the neoplastic cell is unable to complete differentiation and leads to excess proliferation of the leukemic cell line.

U.S. Pat. Nos. 5,369,108, 5,932,616, 5,700,811, 6,087,367 and 6,511,990, and U.S. application Ser. Nos. 10/281,875 filed Oct. 25, 2002, 60/459,826 filed Apr. 1, 2003, 60/510,282 filed Oct. 9, 2003 and 60/525,333 filed Nov. 26, 2003, the contents of which are hereby incorporated by reference, disclose hydroxamic acid derivatives useful for selectively inducing terminal differentiation, cell growth arrest or apoptosis of neoplastic cells. In addition to their biological activity as antitumor agents, these hydroxamic acid derivatives have recently been identified as useful for treating or preventing a wide variety of thioredoxin (TRX)-mediated diseases and conditions, such as inflammatory diseases, allergic diseases, autoimmune diseases, diseases associated with oxidative stress or diseases characterized by cellular hyperproliferation (U.S. application Ser. No. 10/369,094, filed Feb. 15, 2003, the entire content of which is hereby incorporated by reference). Further, these hydroxamic acid derivatives have been identified as useful for treating diseases of the central nervous system (CNS) such as neurodegenerative diseases and for treating brain cancer (See, U.S. application Ser. No. 10/273, 401, filed Oct. 16, 2002, the entire content of which is hereby incorporated by reference).

The inhibition of HDAC by the hydroxamic acid containing compound suberoylanilide hydroxamic acid (SAHA) disclosed in the above referenced U.S. Patents, is thought to occur through direct interaction with the catalytic site of the enzyme as demonstrated by X-ray crystallography studies (Finnin, M. S. et al., Nature 401:188-193 (1999)). The result of HDAC inhibition is not believed to have a generalized effect on the genome, but rather, only affects a small subset of the genome (Van Lint, C. et al., Gene Expression 5:245-53 (1996)). Evidence provided by DNA microarrays using malignant cell lines cultured with a HDAC inhibitor shows that there are a finite (1-2%) number of genes whose products are altered. For example, cells treated in culture with HDAC inhibitors show a consistent induction of the cyclin-dependent kinase inhibitor p21 (Archer, S. Shufen, M. Shei, A., Hodin, R. PNAS 95:6791-96 (1998)). This protein plays an important role in cell cycle arrest. HDAC inhibitors are thought to increase the rate of transcription of p21 by propagating the hyperacetylated state of histones in the region of the p21 gene, thereby making the gene accessible to transcriptional machinery. Genes whose expression is not affected by HDAC inhibitors do not display changes in the acetylation of regional associated histones (Dressel, U. et al., Anticancer Research 20(2A):1017-22 (2000)).

Further, hydroxamic acid derivatives such as SAHA have the ability to induce tumor cell growth arrest, differentiation, and/or apoptosis (Richon et al., Proc. Natl. Acad. Sci. USA, 93:5705-5708 (1996)). These compounds are targeted towards mechanisms inherent to the ability of a neoplastic cell to become malignant, as they do not appear to have toxicity in doses effective for inhibition of tumor growth in animals (Cohen, L. A. et al., Anticancer Research 19:4999-5006 (1999)).

Hydroxamic acid derivatives exhibit several shortcomings, namely their low aqueous solubility and poor cellular permeability, properties that may limit their therapeutic potential.

In view of the wide variety of applications for compounds containing hydroxamic acid moieties, the development of new hydroxamic acid derivatives having improved properties, for example, increased aqueous solubility and cellular permeability, is highly desirable.

SUMMARY OF THE INVENTION

The present invention is directed to prodrugs of hydroxamic acid based histone deacetylase (HDAC) inhibitors, e.g., suberoylanilide hydroxamic acid (SAHA). The prodrugs are acylated derivatives having increased aqueous solubility and cellular permeability as compared with the free hydroxamic acid, and are useful for inhibiting HDACs, and for selectively inducing terminal differentiation, cell growth arrest and/or apoptosis of neoplastic cells, thereby inhibiting proliferation of such cells. Thus, the prodrugs of the present invention are useful in treating a patient having a tumor characterized by proliferation of neoplastic cells. The prodrugs of the invention are also useful in the prevention and treatment of thioredoxin (TRX)-mediated diseases, such as autoimmune, allergic, and inflammatory diseases, and in the prevention and/or treatment of diseases of the central nervous system (CNS), such as neurodegenerative diseases. The present invention further provides pharmaceutical compositions comprising the hydroxamic acid prodrugs, and safe, dosing regimens of these pharmaceutical compositions, which are easy to follow, and which result in a therapeutically effective amount of the active agent in vivo.

The present invention is directed to prodrugs of suberoylanilide hydroxamic acid (SAHA). The prodrugs are acylated derivatives of SAHA having increased cellular permeability as compared with the free hydroxamic acid, and are useful for inhibiting HDACs, and for selectively inducing terminal differentiation, cell growth arrest and/or apoptosis of neoplastic cells, thereby inhibiting proliferation of such cells. Thus, the SAHA prodrugs of the present invention are useful in treating a patient having a tumor characterized by proliferation of neoplastic cells. The SAHA prodrugs of the invention are also useful in the prevention and treatment of TRX-mediated diseases, such as autoimmune, allergic, and inflammatory diseases, and in the prevention and/or treatment of diseases of the CNS, such as neurodegenerative diseases. The present invention further provides pharmaceutical compositions comprising the SAHA prodrug, and safe, dosing regimens of these pharmaceutical compositions, which are easy to follow, and which result in a therapeutically effective amount of SAHA or SAHA prodrug in vivo.

The present invention thus relates to a prodrug of a hydroxamic acid derivative histone deacetylase (HDAC) inhibitor, represented by the structure of formula 1:

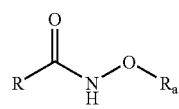

wherein R is a residue of a hydroxamic acid derivative histone deacetylase inhibitor; and $R_a$ is represented by the structure:

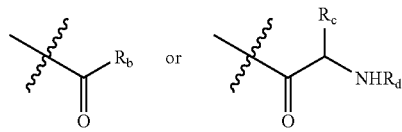

wherein $R_b$ and $R_c$ are independently of each other a hydrogen or an unsubstituted or substituted alkyl, alkenyl, alkynyl, aryl, cycloalkyl, heterocyclyl, heteroaryl, alkylaryl, alkylcycloalkyl, alkylheterocyclyl, alkylheteroaryl or an amino acid residue; and $R_d$ is hydrogen or an amino protecting group;

or a pharmaceutically acceptable salt, hydrate, solvate, polymorph or any combination thereof.

In a further embodiment of formula 1, $R_b$ and $R_c$ are independently of each other a hydrogen, methyl, ethyl, isopropyl, butyl, isobutyl, sec-butyl, t-butyl, phenyl, biphenyl, benzyl, alkylphenyl, napththyl, or pyridyl.

In one embodiment, the prodrug of the present invention is represented by the structure of formula (2):

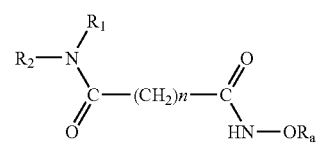

wherein each of $R_1$ and $R_2$ are independently the same as or different from each other and are a hydrogen atom, a hydroxyl group, a substituted or unsubstituted, branched or unbranched alkyl, alkenyl, cycloalkyl, aryl, heterocyclyl, heteroaryl, alkylcycloalkyl, alkylaryl, alkylheterocyclyl, alkylheteroaryl, arylalkyloxy, aryloxy, or pyridine group, or $R_1$ and $R_2$ are bonded together to form a nitrogen containing heterocyclic ring optionally containing one or more additional heteroatoms, and n is an integer of 4 to 8.

In another embodiment, the prodrug of the present invention is represented by the structure of formula (3):

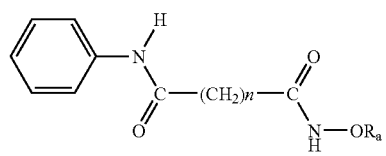

wherein n is an integer of 4 to 8.

In one embodiment of formula (3), n is 6. In accordance with this embodiment, the HDAC inhibitor is a suberoylanilide hydroxamic acid SAHA prodrug, represented by the structure of formula (4):

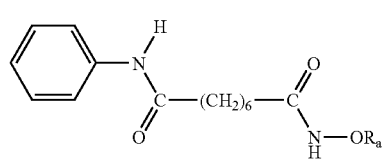

Non-limiting embodiments of SAHA prodrugs are provided in Tables 1 and 2 in the Experimental Details Section.

In another embodiment, the prodrug of the present invention is represented by the structure of formula (5):

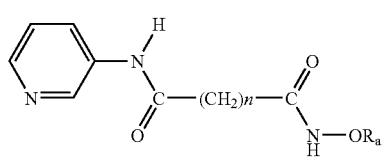
(5)

wherein n is an integer from about 4 to about 8.

In one embodiment of formula (5), n is 6. In accordance with this embodiment, the HDAC inhibitor is a pyroxamide prodrug, represented by the structure of formula (6):

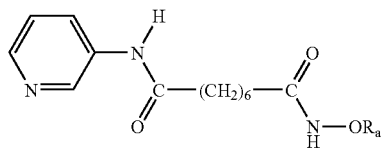
(6)

In another embodiment, the prodrug of the present invention is represented by the structures of formula (9) or (10), i.e., a prodrug of m-carboxycinnamic acid bishydroxamide (CBHA):

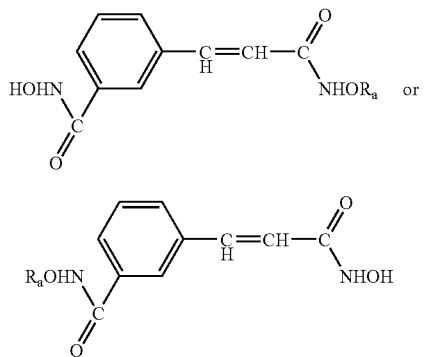
(9)

or (10)

In another embodiment, the prodrug of the present invention is represented by the structure of formula (9):

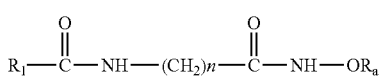
(11)

wherein $R_1$ is a substituted or unsubstituted phenyl, piperidine, thiazole, 2-pyridine, 3-pyridine or 4-pyridine and n is an integer of 4 to 8.

In another embodiment, the prodrug of the present invention is represented by the structure of formula (12):

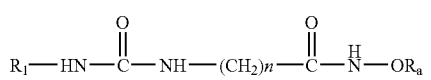
(12)

wherein $R_1$ is a substituted or unsubstituted phenyl, piperidine, thiazole, 2-pyridine, 3-pyridine or 4-pyridine and n is an integer of 4 to 8.

In another embodiment, the prodrug of the present invention is represented by the structure of formula (13):

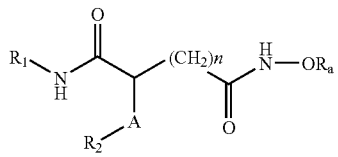
(13)

wherein A is an amide moiety, $R_1$ and $R_2$ are each selected from substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; and n is an integer of 3 to 10.

In another embodiment, the prodrug of the present invention is represented by the structure of formula (13a), wherein $R_1$ and $R_2$ have the meaning as set forth for formula (13).

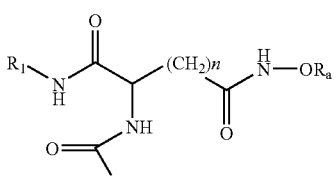
(13a)

In another embodiment, the prodrug of the present invention is represented by the structure of formula (13b), wherein $R_1$ and $R_2$ have the meaning as set forth for formula (13).

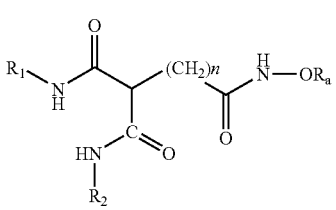
(13b)

In another embodiment, the prodrug of the present invention is represented by the structure of formula (14):

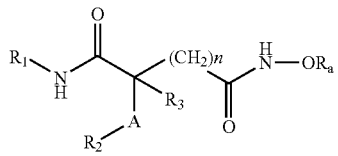
(14)

wherein A is an amide moiety, $R_1$ and $R_2$ are each selected from substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; $R_3$ is hydrogen, a halogen, a phenyl or a cycloalkyl moiety and n is an integer of 3 to 10.

In another embodiment, the prodrug of the present invention is represented by the structure of formula (14a), wherein $R_1$ and $R_2$ have the meaning as set forth for formula (14), and n is an integer from about 3 to 10.

(14a)
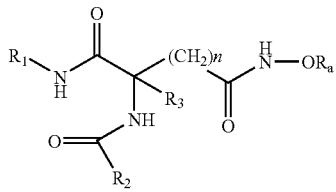

In another embodiment, the prodrug of the present invention is represented by the structure of formula (14b), wherein $R_1$ and $R_2$ have the meaning as set forth for formula (14), and n is an integer from about 3 to 10.

(14b)
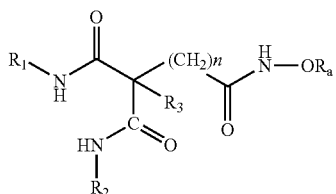

In another embodiment, the prodrug of the present invention is represented by the structure of formula (15):

(15)
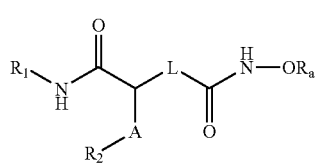

wherein L is a linker selected from the group consisting of an amide moiety, O—, —S—, —NH—, NR, —CH$_2$—, —(CH$_2$)$_p$—, —(CH=CH)—, phenylene, cycloalkylene, or any combination thereof wherein R is a substituted or unsubstituted $C_1$-$C_5$ alkyl; and wherein each of $R_1$ and $R_2$ are independently a substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; p is an integer of 0 to 10.

In another embodiment, the prodrug of the present invention is represented by the structure of formula (15a), wherein $R_1$ and $R_2$ have the meaning as set forth for formula (15).

(15a)
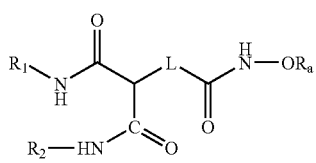

In another embodiment, the prodrug of the present invention is represented by the structure of formula (15b), wherein $R_1$ and $R_2$ have the meaning as set forth for formula (15).

(15b)
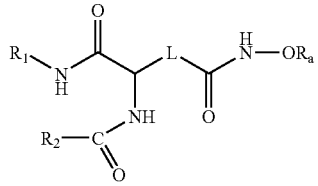

In another embodiment, the prodrug of the present invention is represented by the structure of formula (29):

(29)
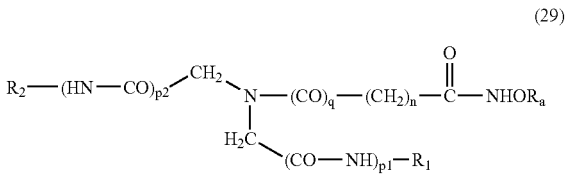

wherein
n is 2, 3, 4, 5, 6, 7 or 8;
q is 0 or 1;
$p_1$ and $p_2$ are independently of each other 0 or 1;
$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or when $p_1$ and $p_2$ are both 0, $R_1$ and $R_2$ together with the —CH$_2$—N—CH$_2$— group to which they are attached can also represent a nitrogen-containing heterocyclic ring; or when at least one of $p_1$ and $p_2$ is not 0, $R_1$ or $R_2$ or both can also represent hydrogen or alkyl.

In another embodiment, the prodrug of the present invention is represented by the structure of formula (30):

(30)
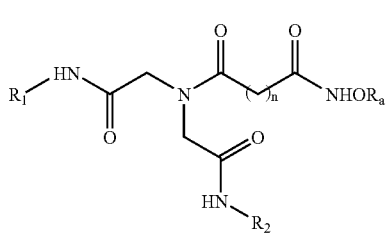

wherein
n is 2, 3, 4, 5, 6, 7 or 8;
$R_1$ and $R_2$ are independently of each other a hydrogen or an unsubstituted or substituted alkyl, aryl, heteroaryl, cycloalkyl, heterocyclyl, alkylaryl, alkylheteroaryl, alkylcycloalkyl or alkylheterocyclyl;
and pharmaceutically acceptable salts, solvates, hydrates, prodrugs and polymorphs thereof.

In another embodiment, the prodrug of the present invention is represented by the structure of formula (31):

(31)
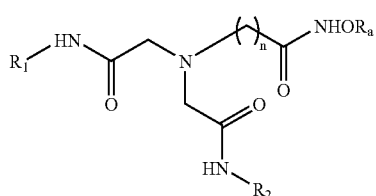

wherein
n is 2, 3, 4, 5, 6, 7 or 8;
$R_1$ and $R_2$ are independently of each other a hydrogen or an unsubstituted or substituted alkyl, aryl, heteroaryl, cycloalkyl, heterocyclyl, alkylaryl, alkylheteroaryl, alkylcycloalkyl or alkylheterocyclyl.

In another embodiment, the prodrug of the present invention is represented by the structure of formula (32):

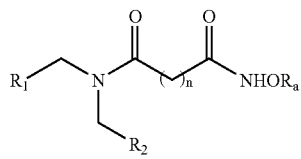

(32)

wherein
n is 2, 3, 4, 5, 6, 7 or 8;
$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or $R_1$ and $R_2$ together with the —$CH_2$—N—$CH_2$— group to which they are attached can also represent a nitrogen-containing heterocyclic ring.

In another embodiment, the prodrug of the present invention is represented by the structure of formula (33):

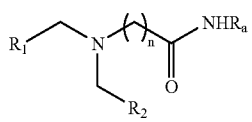

(33)

wherein
n is 2, 3, 4, 5, 6, 7 or 8;
$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or $R_1$ and $R_2$ together with the —$CH_2$—N—$CH_2$— group to which they are attached can also represent a nitrogen-containing heterocyclic ring.

In another embodiment, the prodrug of the present invention is represented by the structure of formula (34):

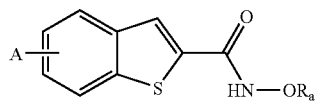

(34)

wherein A is alkyl, aryl or a group selected from

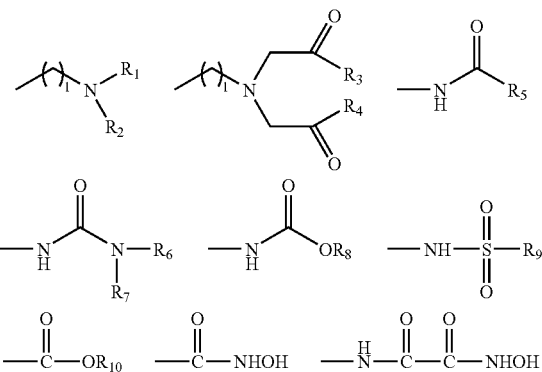

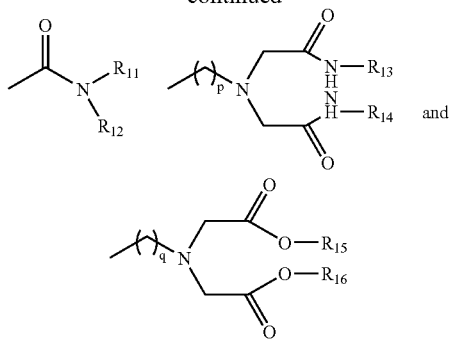

wherein $R_1$-$R_{16}$ are independently of each other a hydrogen or an unsubstituted or substituted alkyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring; and
l, p and q are independently of each other 0, 1 or 2.

In another embodiment, the prodrug of the present invention is represented by the structure of formula (36):

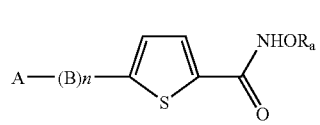

(36)

wherein
A is alkyl, aryl or a group selected from:

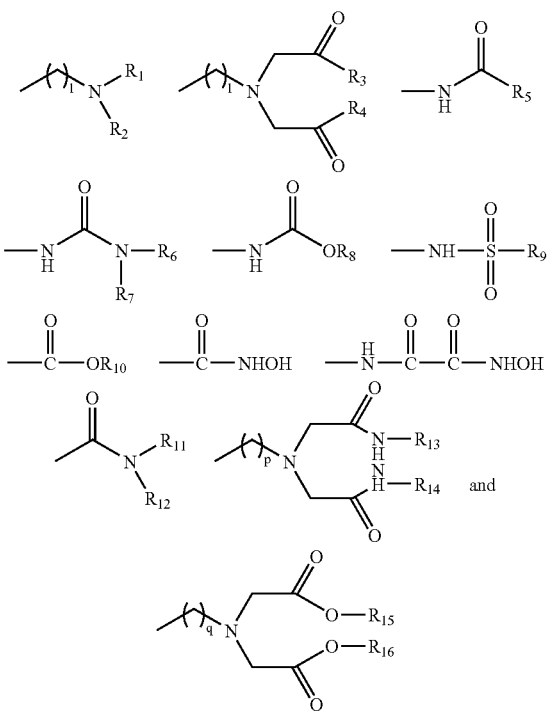

wherein $R_1$-$R_{16}$ are independently of each other a hydrogen or an unsubstituted or substituted alkyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$, and $R_{12}$, together with the nitrogen atom to which they are attached, form a nitrogen-containing heterocyclic ring;

B is

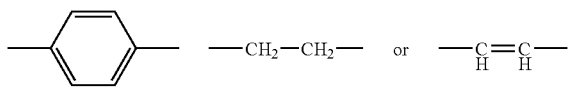

n is 0 or 1; and l, p and q are independently of each other 0, 1 or 2.

As demonstrated herein, the hydroxamic acid derivative prodrugs of the present invention show improved solubility and cellular permeability as compared to the free hydroxamic acid derivatives, and are histone deacetylase (HDAC) inhibitors. Accordingly, in one embodiment, the invention relates to a method of inhibiting the activity of a histone deacetylase comprising contacting the histone deacetylase with an effective amount of one or more of the hydroxamic acid prodrugs described herein.

The invention also relates to methods of using the hydroxamic acid prodrugs described herein, for prevention and/or treatment of the diseases and disorders described herein such as cancer, TRX-mediated diseases such as autoimmune, allergic and inflammatory diseases, and diseases of the central nervous system (CNS), such as neurodegenerative diseases.

In a particular embodiment, the invention relates to a method of treating cancer in a subject in need of treatment comprising administering to said subject a therapeutically effective amount of one or more of the hydroxamic acid prodrugs described herein. Non-limiting examples of cancers are: acute leukemias such as acute lymphocytic leukemia (ALL) and acute myeloid leukemia (AML); chronic leukemia such as chronic lymphocytic leukemia (CLL) and chronic myelogenous leukemia (CML), Hairy Cell Leukemia, cutaneous T-cell lymphoma (CTCL), noncutaneous peripheral T-cell lymphoma, lymphoma associated with human T-cell lymphotrophic virus (HTLV) such as adult T-cell leukemia/lymphoma (ATLL), Hodgkin's disease, non-Hodgkin's lymphoma, large-cell lymphoma, diffuse large B-cell lymphoma (DLBCL); Burkitt's lymphoma; primary central nervous system (CNS) lymphoma; multiple myeloma; childhood solid tumors such as brain tumor, neuroblastoma, retinoblastoma, Wilm's tumor, bone tumor, soft-tissue sarcoma, head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In another embodiment, the hydroxamic acid prodrugs are used in a method of treating a thioredoxin (TRX)-mediated disease or disorder such as autoimmune, allergic and inflammatory diseases in a subject in need thereof, comprising administering to the subject a therapeutically effective amount of one or more of the hydroxamic acid prodrugs described herein.

In another embodiment, the hydroxamic acid prodrugs are used in a method of treating a disease of the central nervous system (CNS) in a subject in need thereof comprising administering to the subject a therapeutically effective amount of any one or more of the hydroxamic acid prodrugs described herein. In particular embodiments, the CNS disease is a neurodegenerative disease. In further embodiments, the neurodegenerative disease is an inherited neurodegenerative disease, such as those inherited neurodegenerative diseases that are polyglutamine expansion diseases.

The invention further relates to use of the hydroxamic acid prodrugs for the manufacture of a medicament for the prevention and/or treatment of the diseases and disorders described herein such as cancer, TRX-mediated diseases such as autoimmune, allergic and inflammatory diseases, and diseases of the central nervous system (CNS), such as neurodegenerative diseases.

In another embodiment, the invention relates to methods of using the hydroxamic acid prodrugs of the present invention for inducing terminal differentiation, cell growth arrest, and/or apoptosis of neoplastic cells thereby inhibiting the proliferation of such cells. The methods can be practiced in vivo or in vitro.

In one embodiment, the present invention provides in vivo methods for selectively inducing terminal differentiation, cell growth arrest and/or apoptosis of neoplastic cells in a subject, thereby inhibiting proliferation of such cells in said subject, by administering to the subject an effective amount of any one or more of the hydroxamic acid prodrugs described herein.

In a particular embodiment, the present invention relates to a method of selectively inducing terminal differentiation of neoplastic cells and thereby inhibiting proliferation of such cells in a subject. The method comprises administering to the subject an effective amount of one or more of the hydroxamic acid prodrugs described herein.

In another embodiment, the invention relates to a method of selectively inducing cell growth arrest of neoplastic cells and thereby inhibiting proliferation of such cells in a subject. The method comprises administering to the subject an effective amount of one or more of the hydroxamic acid prodrugs described herein.

In another embodiment, the invention relates to a method of selectively inducing apoptosis of neoplastic cells and thereby inhibiting proliferation of such cells in a subject. The method comprises administering to the subject an effective amount of one or more of the hydroxamic acid prodrugs described herein.

In another embodiment, the invention relates to a method of treating a patient having a tumor characterized by proliferation of neoplastic cells. The method comprises administering to the patient one or more of the hydroxamic acid prodrugs described herein. The amount of prodrug is effective to selectively induce terminal differentiation, induce cell growth arrest and/or induce apoptosis of such neoplastic cells and thereby inhibit their proliferation.

The present invention also provides in vitro methods for selectively inducing terminal differentiation, cell growth arrest and/or apoptosis of neoplastic cells, thereby inhibiting proliferation of such cells, by contacting the cells with an effective amount of any one or more of the hydroxamic acid prodrugs described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the hydroxamic acid prodrugs described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the hydroxamic acid prodrugs described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the hydroxamic acid prodrugs described herein.

In another embodiment, the invention relates to an in vitro method of inducing terminal differentiation of tumor cells in a tumor comprising contacting the cells with an effective amount of any one or more of the hydroxamic acid prodrugs described herein.

The invention also relates to a pharmaceutical composition comprising a therapeutically effective amount of any one of the hydroxamic acid prodrugs and a pharmaceutically acceptable carrier. Thus, in further embodiments, the methods of the present invention comprise administering the hydroxamic acid prodrugs as a pharmaceutical composition comprising the hydroxamic acid prodrugs, and a pharmaceutically acceptable carrier. The hydroxamic acid prodrugs can be administered in a total daily dose of up to 800 mg, preferably orally, once, twice or three times daily, continuously (i.e., every day) or intermittently (e.g., 3-5 days a week).

The prodrugs of the present invention can be administered in a total daily dose that may vary from patient to patient, and may be administered at varying dosage schedules. Suitable dosages are total daily dosage of between about 25-4000 mg/m$^2$ administered orally once-daily, twice-daily or three times-daily, continuous (every day) or intermittently (e.g., 3-5 days a week). Furthermore, the compositions may be administered in cycles, with rest periods in between the cycles (e.g., treatment for two to eight weeks with a rest period of up to a week between treatments).

The foregoing and other objects, features and advantages of the invention will be apparent from the following more particular description of preferred embodiments of the invention.

DETAILED DESCRIPTION OF THE INVENTION

The present invention is directed to prodrugs of hydroxamic acid based histone deacetylase (HDAC) inhibitors, e.g., suberoylanilide hydroxamic acid (SAHA). The prodrugs are acylated derivatives having increased aqueous solubility and cellular permeability as compared with the free hydroxamic acid, and are useful for inhibiting HDACs, and for selectively inducing terminal differentiation, cell growth arrest and/or apoptosis of neoplastic cells, thereby inhibiting proliferation of such cells. Thus, the prodrugs of the present invention are useful in treating a patient having a tumor characterized by proliferation of neoplastic cells. The prodrugs of the invention are also useful in the prevention and treatment of thioredoxin (TRX)-mediated diseases, such as autoimmune, allergic and inflammatory diseases, and in the prevention and/or treatment of diseases of the central nervous system (CNS), such as neurodegenerative diseases. The present invention further provides pharmaceutical compositions comprising the hydroxamic acid prodrugs, and safe, dosing regimens of these pharmaceutical compositions, which are easy to follow, and which result in a therapeutically effective amount of the active agent in vivo.

The present invention is directed to prodrugs of suberoylanilide hydroxamic acid (SAHA). The prodrugs are acylated derivatives of SAHA having increased cellular permeability as compared with the free hydroxamic acid, and are useful for inhibiting HDACs, and for selectively inducing terminal differentiation, cell growth arrest and/or apoptosis of neoplastic cells, thereby inhibiting proliferation of such cells. Thus, the SAHA prodrugs of the present invention are useful in treating a patient having a tumor characterized by proliferation of neoplastic cells. The SAHA prodrugs of the invention are also useful in the prevention and treatment of TRX-mediated diseases, such as autoimmune, allergic and inflammatory diseases, and in the prevention and/or treatment of diseases of the CNS, such as neurodegenerative diseases. The present invention further provides pharmaceutical compositions comprising the SAHA prodrug, and safe, dosing regimens of these pharmaceutical compositions, which are easy to follow, and which result in a therapeutically effective amount of SAHA or SAHA prodrug in vivo.

For purposes of this specification the term "prodrug" is defined as a derivative of the active form of a compound or composition which derivative, when administered to a mammal is gradually converted to the active form.

In one embodiment, the prodrugs produce an equal or better therapeutic response and/or a reduced toxicity level compared to the free hydroxamic acids.

In one embodiment, the hydroxamic acid prodrugs of the present invention, when administered to a mammal, are converted in-vivo to the free hydroxamic acid. The prodrugs have increased aqueous solubility and enhanced cellular permeability as compared to the free hydroxamic acid, thus facilitating the delivery of the active agent to its cellular target.

However, it is also contemplated that the hydroxamic acid prodrugs themselves are the active agent, and are thus useful for inhibiting HDACs, for selectively inducing terminal differentiation, cell growth arrest and/or apoptosis of neoplastic cells, for treating cancer, TRX-mediated diseases and diseases of the CNS. Accordingly, the present invention also encompasses the use of the hydroxamic acid prodrugs as the active agents, i.e., the prodrug is delivered to the cellular target intact.

Compounds

The present invention thus relates to a prodrug of a hydroxamic acid derivative histone deacetylase (HDAC) inhibitor, represented by the structure of formula 1:

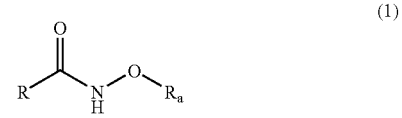

(1)

wherein R is a residue of a hydroxamic acid derivative histone deacetylase inhibitor; and $R_a$ is represented by the structure:

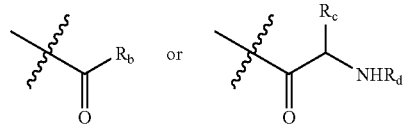

wherein $R_b$ and $R_c$ are independently of each other a hydrogen or an unsubstituted or substituted alkyl, alkenyl, alkynyl, aryl, cycloalkyl, heterocyclyl, heteroaryl, alkylaryl, alkylcycloalkyl, alkylheterocyclyl, alkylheteroaryl or an amino acid residue; and $R_d$ is hydrogen or an amino protecting group;

or a pharmaceutically acceptable salt, hydrate, solvate, polymorph or any combination thereof.

Specific non-limiting examples of $R_a$ are:

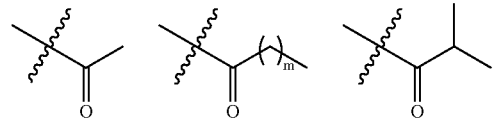

-continued

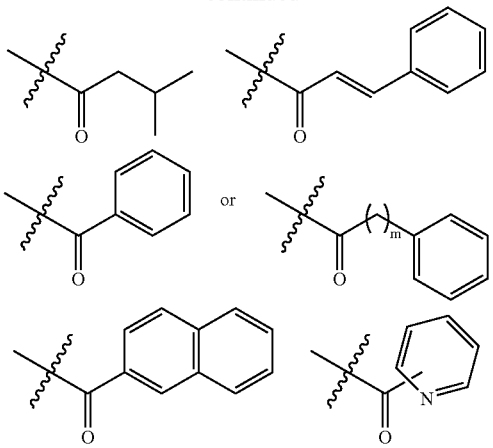

wherein m is an integer of 1 to 10, e.g., 1, 2, 3, 4, 5, 6, 7, 8, 9 or 10.

In another embodiment of formula (1), $R_a$ is represented by the structure:

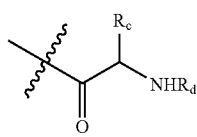

wherein $R_d$ hydrogen or an amino protecting group.

In a further embodiment of formula 1, $R_b$ or $R_d$ are independently of each other hydrogen, methyl, ethyl, isopropyl, butyl, isobutyl, sec-butyl, t-butyl, phenyl, benzyl, alkylphenyl, napththyl or pyridyl.

Other examples of suitable substituents for $R_a$-$R_d$ are provided in the Experimental Details section.

In one embodiment, the prodrug of the present invention is represented by the structure of formula (2):

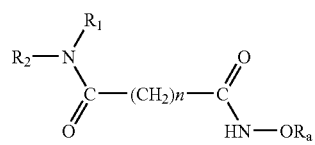

(2)

wherein each of $R_1$ and $R_2$ are independently the same as or different from each other and are a hydrogen atom, a hydroxyl group, a substituted or unsubstituted, branched or unbranched alkyl, alkenyl, cycloalkyl, aryl, heterocyclyl, heteroaryl, alkylcycloalkyl, alkylaryl, alkylheterocyclyl, alkylheteroaryl, arylalkyloxy, aryloxy, or pyridine group, or $R_1$ and $R_2$ are bonded together to form a nitrogen containing heterocyclic ring optionally containing one or more additional heteroatoms, and n is an integer of 4 to 8.

In a particular embodiment of formula (2), n is an integer from 5 to 7. In another particular embodiment of formula 2, n is 6.

In yet another embodiment of formula (2), $R_1$ is a hydrogen atom, $R_2$ is a substituted or unsubstituted phenyl and n is 6.

In yet another embodiment of formula (2), $R_1$ is a hydrogen atom, $R_2$ is a substituted phenyl and n is 6, wherein the phenyl substituent is selected from the group consisting of a methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methoxy, phenyloxy, benzyloxy, phenylaminooxy, phenylaminocarbonyl, methoxycarbonyl, methylaminocarbonyl, dimethylamino, dimethylamino carbonyl, or hydroxylaminocarbonyl group.

In another embodiment of formula (2), n is 6, $R_1$ is a hydrogen atom and $R_2$ is a cyclohexyl group. In another embodiment of formula (2), n is 6, $R_1$ is a hydrogen atom and $R_2$ is a methoxy group. In another embodiment of formula (2), n is 6 and $R_1$ and $R_2$ bond together to form a piperidine group. In another embodiment of formula (2), n is 6, $R_1$ is a hydrogen atom and $R_2$ is a benzyloxy group. In another embodiment of formula (2), $R_1$ is a hydrogen atom and $R_2$ is a γ-pyridine group. In another embodiment of formula (2), $R_1$ is a hydrogen atom and $R_2$ is a β-pyridine group. In another embodiment of formula (2), $R_1$ is a hydrogen atom and $R_2$ is an α-pyridine group. In another embodiment of formula (2), n is 6, and $R_1$ and $R_2$ are both methyl groups. In another embodiment of formula (2), n is 6, $R_1$ is a methyl group and $R_2$ is a phenyl group.

In another embodiment, the prodrug of the present invention is represented by the structure of formula (3):

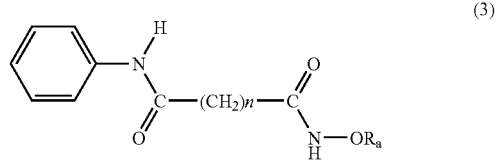

(3)

wherein n is an integer of 4 to 8.

In one embodiment, n of compound (3) is 6. In accordance with this embodiment, the prodrug of the present invention is represented by the structure of formula (4), i.e., a prodrug of suberoylanilide hydroxamic acid (SAHA):

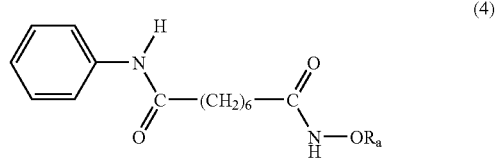

(4)

Non-limiting embodiments of SAHA prodrugs are provided in Tables 1 and 2 in the Experimental Details Section.

In another embodiment, the prodrug of the present invention is represented by the structure of formula (5):

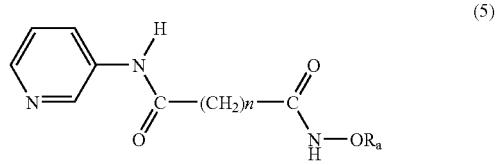

(5)

wherein n is an integer from about 4 to about 8.

In one embodiment, n in compound (5) is 6. In accordance with this embodiment, the prodrug of the present invention is represented by the structure of formula (6), i.e., a prodrug of pyroxamide:

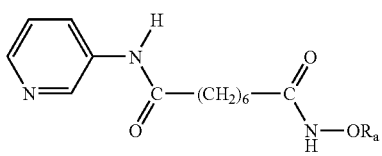
(6)

In another embodiment, the prodrug of the present invention is represented by the structure of formula (7):

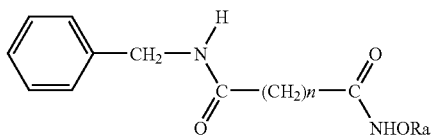
(7)

wherein n is an integer of 4 to 8.

In another embodiment, the prodrug of the present invention is represented by the structure of formula (8):

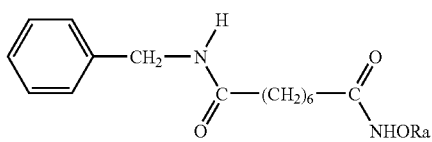
(8)

In another embodiment, the prodrug of the present invention is represented by the structures of formula (9) or (10), i.e., a prodrug of m-carboxycinnamic acid bishydroxamide (CBHA):

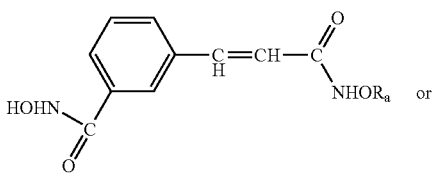
(9)

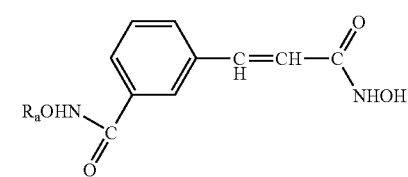
(10)

In another embodiment, the prodrug of the present invention is represented by the structure of formula (11):

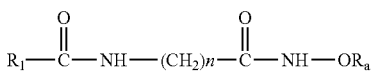
(11)

wherein $R_1$ is a substituted or unsubstituted phenyl, piperidine, thiazole, 2-pyridine, 3-pyridine or 4-pyridine and n is an integer of 4 to 8.

In one particular embodiment of formula (11), R is a substituted phenyl group. In another particular embodiment of formula (11), R is a substituted phenyl group, where the substituent is selected from the group consisting of methyl, cyano, nitro, thio, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methyloxy, phenyloxy, benzyloxy, phenylaminooxy, phenylaminocarbonyl, methyloxycarbonyl, methylaminocarbonyl, dimethylamino, dimethylaminocarbonyl, or hydroxylaminocarbonyl group.

In another particular embodiment of formula (11), R is a substituted or unsubstituted 2-pyridine, 3-pyridine or 4-pyridine and n is an integer from about 4 to about 8.

In another embodiment, the prodrug of the present invention is represented by the structure of formula (12):

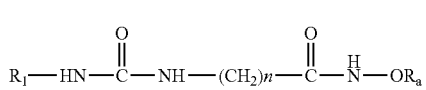
(12)

wherein $R_1$ is a substituted or unsubstituted phenyl, piperidine, thiazole, 2-pyridine, 3-pyridine or 4-pyridine and n is an integer of 4 to 8.

In a particular embodiment of formula (12), R is a substituted phenyl group. In another particular embodiment of formula (12), R is a substituted phenyl group, where the substituent is selected from the group consisting of methyl, cyano, nitro, thio, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methyloxy, phenyloxy, benzyloxy, phenylaminooxy, phenylaminocarbonyl, methyloxycarbonyl, methylaminocarbonyl, dimethylamino, dimethylaminocarbonyl, or hydroxylaminocarbonyl group.

In another particular embodiment of formula (12), R is phenyl and n is 5. In another embodiment, n is 5 and R is 3-chlorophenyl.

In another embodiment, the prodrug of the present invention is represented by the structure of formula (13):

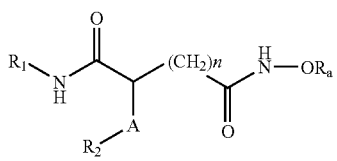
(13)

wherein A is an amide moiety, $R_1$ and $R_2$ are each selected from substituted or unsubstituted aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, or quinolinyl or isoquinolinyl; n is an integer from about 3 to about 10.

In one embodiment of formula (13), the prodrug of the present invention is represented by the structure of formula (13a), wherein $R_1$ and $R_2$ have the meaning as set forth for formula (13).

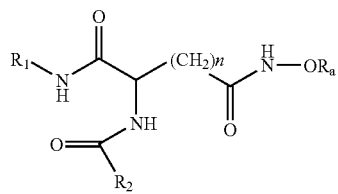

(13a)

In another embodiment of formula (13), the prodrug of the present invention is represented by the structure of formula (13b), wherein $R_1$ and $R_2$ have the meaning as set forth for formula (13).

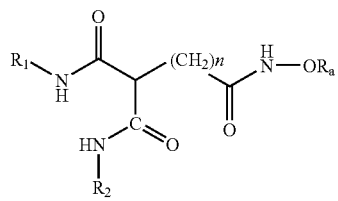

(13b)

In certain embodiments of formulas (13), (13a) and (13b), $R_1$ is —NH—$R_4$ wherein $R_4$ is substituted or unsubstituted, aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl.

In another embodiment, the prodrug of the present invention is represented by the structure of formula (14):

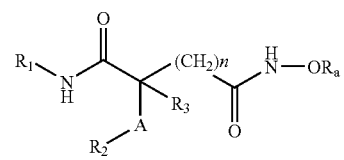

(14)

wherein A is an amide moiety, $R_1$ and $R_2$ are each selected from substituted or unsubstituted aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, or quinolinyl or isoquinolinyl; $R_3$ is hydrogen, a halogen, a phenyl or a cycloalkyl moiety and n is an integer of 3 to 10.

In another embodiment of formula (14), the prodrug of the present invention is represented by the structure of formula (14a), wherein $R_1$ and $R_2$ have the meaning as set forth for formula (14), and n is an integer from about 3 to 10.

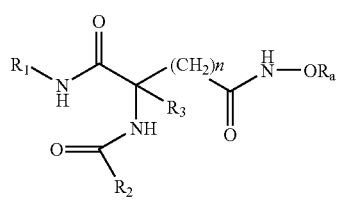

(14a)

In another embodiment of formula (14), the prodrug of the present invention is represented by the structure of formula (14b), wherein $R_1$ and $R_2$ have the meaning as set forth for formula (14), and n is an integer from about 3 to 10.

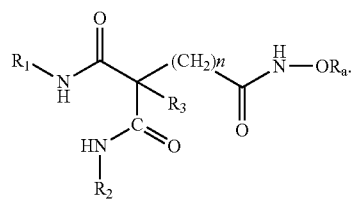

(14b)

In another embodiment, the prodrug of the present invention is represented by the structure of formula (15):

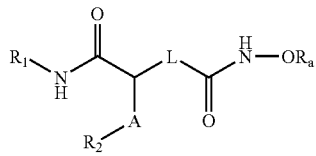

(15)

wherein L is a linker selected from the group consisting of an amide moiety, O—, —S—, —NH—, NR, —CH$_2$—, —(CH$_2$)$_p$—, —(CH═CH)—, phenylene, cycloalkylene, or any combination thereof wherein R is a substituted or unsubstituted $C_1$-$C_5$ alkyl; and wherein each of $R_1$ and $R_2$ are independently a substituted or unsubstituted aryl (e.g., phenyl), arylalkyl (e.g., benzyl), naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; p is an integer of 0 to 10.

In another embodiment of formula (15), the prodrug of the present invention is represented by the structure of formula (15a), wherein $R_1$ and $R_2$ have the meaning as set forth for formula (15).

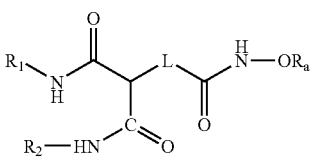

(15a)

In another embodiment, the prodrug of the present invention is represented by the structure of formula (15b), wherein $R_1$ and $R_2$ have the meaning as set forth for formula (15).

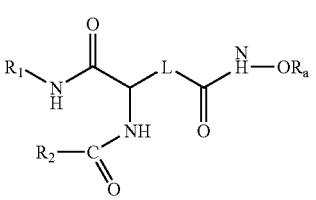

(15b)

For example, the prodrug of the present invention can be represented by any one or more of the following structures:

(16)

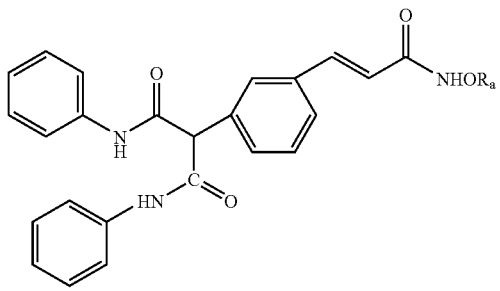

A compound represented by the structure:

(17)

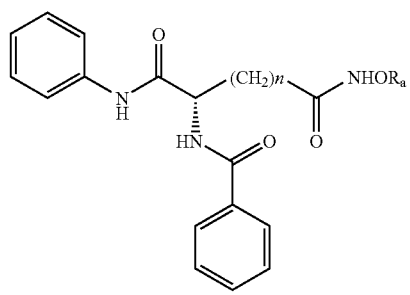

wherein n is an integer of 3 to 10, or an enantiomer thereof. In one particular embodiment of formula (17), n=5.

A compound represented by the structure:

(18)

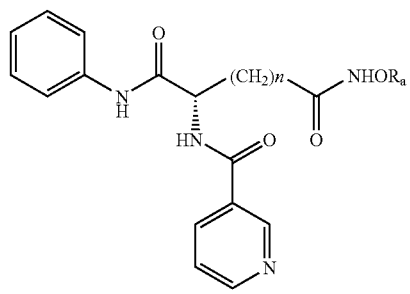

wherein n is an integer of 3 to 10, or an enantiomer thereof. In one particular embodiment of formula (18), n=5.

A compound represented by the structure:

(19)

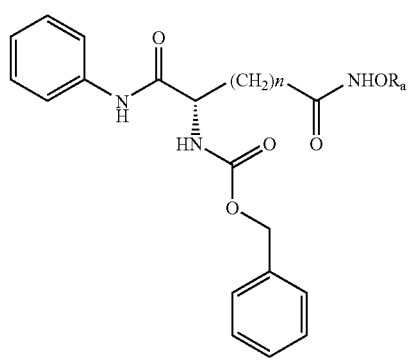

wherein n is an integer of 3 to 10 or an enantiomer thereof. In one particular embodiment of formula (19), n=5.

A compound represented by the structure:

(20)

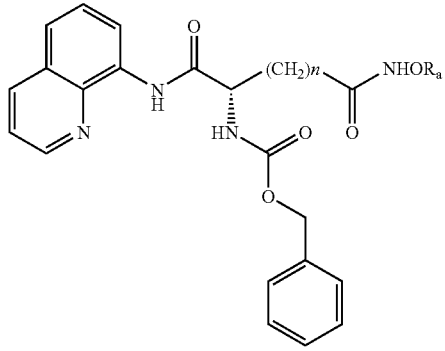

wherein n is an integer of 3 to 10, or an enantiomer thereof. In one particular embodiment of formula (20), n=5.

A compound represented by the structure:

(21)

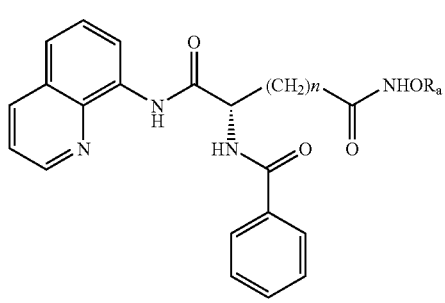

wherein n is an integer of 3 to 10 or an enantiomer thereof. In one particular embodiment of the formula (21), n=5.

A compound represented by the structure:

(22)

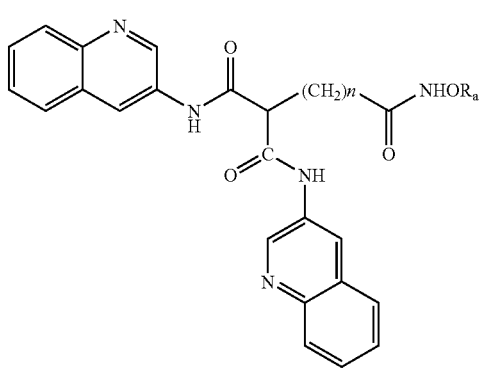

wherein n is an integer of 3 to 10, or an enantiomer thereof. In one particular embodiment of formula (22), n=5.

A compound represented by the structure:

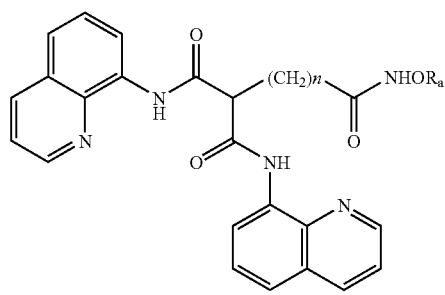
(23)

wherein n is an integer of 3 to 10 or an enantiomer thereof. In one particular embodiment of formula (23), n=5.

A compound represented by the structure:

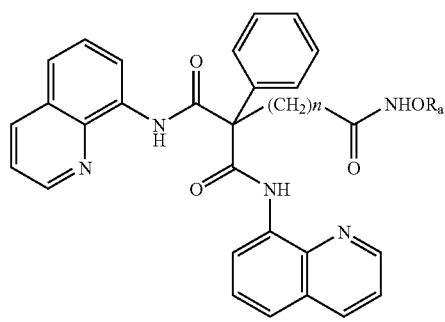
(24)

wherein n is an integer of 3 to 10, or an enantiomer thereof. In one particular embodiment of formula (24), n=5.

A compound represented by the structure:

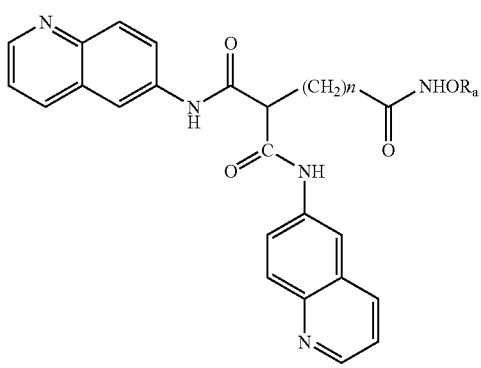
(25)

wherein n is an integer of 3 to 10, or an enantiomer thereof. In one particular embodiment of formula (25), n=5.

A compound represented by the structure:

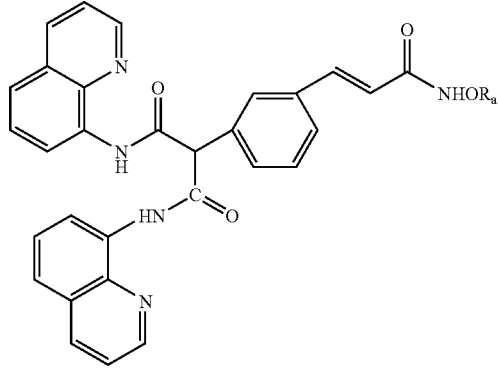
(26)

wherein n is an integer of 3 to 10, or an enantiomer thereof. In one particular embodiment of formula (26), n=5.

A compound represented by the structure:

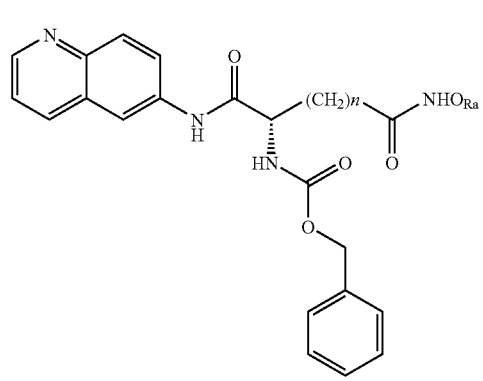
(27)

wherein n is an integer of 3 to 10, or an enantiomer thereof. In one particular embodiment of formula (27), n=5.

A compound represented by the structure:

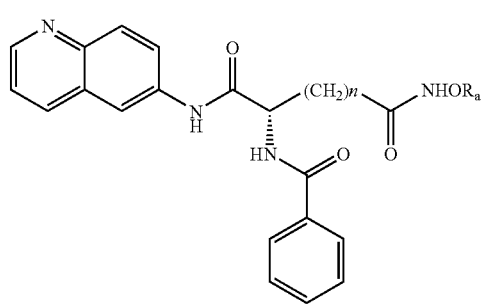
(28)

In another embodiment, the prodrug of the present invention is represented by the structure of formula (29):

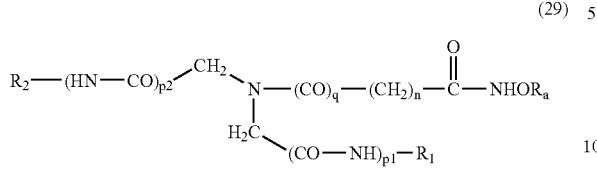

(29)

wherein
n is 2, 3, 4, 5, 6, 7 or 8;
q is 0 or 1;
$p_1$ and $p_2$ are independently of each other 0 or 1;
$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or when $p_1$ and $p_2$ are both 0, $R_1$ and $R_2$ together with the —$CH_2$—N—$CH_2$— group to which they are attached can also represent a nitrogen-containing heterocyclic ring; or when at least one of $p_1$ and $p_2$ is not 0, $R_1$ or $R_2$ or both can also represent hydrogen or alkyl.

In one particular embodiment of formula (29), $p_1$ and $p_2$ are both 0. In another embodiment of formula (29), q is 0. In another embodiment of Formula I, q is 1. In another embodiment of formula (29), n is 5. In yet another embodiment of formula (29), n is 6.

In another embodiment, the prodrug of the present invention is represented by the structure of formula (30):

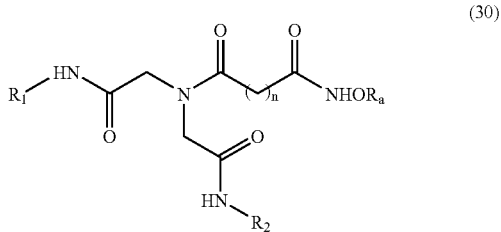

(30)

wherein
n is 2, 3, 4, 5, 6, 7 or 8;
$R_1$ and $R_2$ are independently of each other a hydrogen or an unsubstituted or substituted alkyl, aryl, heteroaryl, cycloalkyl, heterocyclyl, alkylaryl, alkylheteroaryl, alkylcycloalkyl or alkylheterocyclyl;
and pharmaceutically acceptable salts, solvates, hydrates, prodrugs and polymorphs thereof.

In one embodiment of formula (30), n is 5. In another embodiment of formula (30), n is 6.

In another embodiment, the prodrug of the present invention is represented by the structure of formula (31):

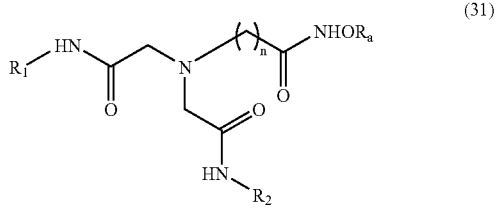

(31)

wherein
n is 2, 3, 4, 5, 6, 7 or 8;
$R_1$ and $R_2$ are independently of each other a hydrogen or an unsubstituted or substituted alkyl, aryl, heteroaryl, cycloalkyl, heterocyclyl, alkylaryl, alkylheteroaryl, alkylcycloalkyl or alkylheterocyclyl.

In one embodiment of formula (31), n is 5. In another embodiment of formula (31), n is 6.

In another embodiment, the prodrug of the present invention is represented by the structure of formula (32):

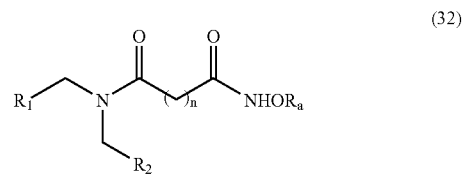

(32)

wherein
n is 2, 3, 4, 5, 6, 7 or 8;
$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or $R_1$ and $R_2$ together with the —$CH_2$—N—$CH_2$— group to which they are attached can also represent a nitrogen-containing heterocyclic ring.

In one embodiment of formula (32), n is 5. In another embodiment of formula (32), n is 6.

In another embodiment, the prodrug of the present invention is represented by the structure of formula (33):

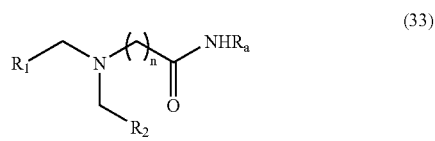

(33)

wherein
n is 2, 3, 4, 5, 6, 7 or 8;
$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or $R_1$ and $R_2$ together with the —$CH_2$—N—$CH_2$— group to which they are attached can also represent a nitrogen-containing heterocyclic ring.

In one embodiment of formula (33), n is 5. In another embodiment of formula (33), n is 6.

In further particular embodiments of Formulas (29)-(33), at least one of $R_1$ and $R_2$ is an unsubstituted or substituted phenyl, benzyl, alkylphenyl, naphthyl, biphenyl, —CH(Ph)$_2$, —CH=CHPh, cyclohexyl, alkylcyclohexyl, quinolinyl, alkylquinolinyl, isoquinolinyl, alkylisoquinolinyl, tetrahydroquinolinyl, alkyltetrahydroquinolinyl, tetrahydroisoquinolinyl, alkyltetrahydroisoquinolinyl, indazolyl, alkylindazolyl, benzothiazolyl, alkylbenzothiazolyl, indolyl, alkylindolyl, piperazinyl, alkyklpiperazinyl, morpholinyl, alkylmorpholinyl, piperidinyl, alkylpiperidinyl, pyridyl or alkylpyridyl.

Furthermore, in one particular embodiment of Formulas (30) or (31), $R_1$ and $R_2$ is a hydrogen, methyl, ethyl, propyl, isopropyl, butyl, isobutyl sec-butyl or tert-butyl.

Furthermore, in one particular embodiment of formulas (32) or (33), $R_1$ and $R_2$ together with the —$CH_2$—N—$CH_2$— group to which they are attached represent a nitrogen-containing heterocyclic ring. Examples of nitrogen-containing heterocylic rings include but are not limited to piperazine, piperidine, morpholine, tetrahydroquinoline, tetrahydroisoquinoline and the like.

Specific embodiments depicting non-limiting examples of the iminodiacetic acid hydroxamic acid derivatives which can suitably form prodrug derivatives of the present invention are disclosed in U.S. Pat. No. 6,511,990, and in U.S. application Ser. No. 10/281,875 filed Oct. 25, 2002 and 60/459,826 filed Apr. 1, 2003, the contents of which are hereby incorporated by reference herein.

In another embodiment, the prodrug of the present invention is represented by the structure of formula (34):

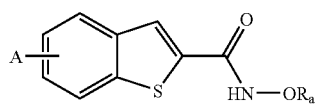
(34)

wherein A is alkyl, aryl or a group selected from

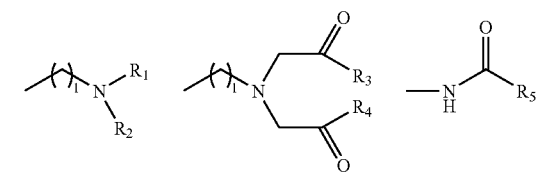

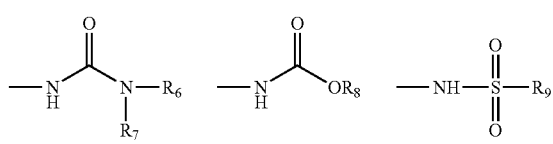

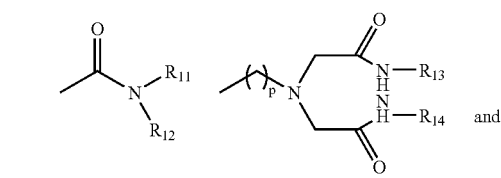

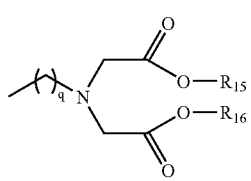

wherein $R_1$-$R_{16}$ are independently of each other a hydrogen or an unsubstituted or substituted alkyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring; and l, p and q are independently of each other 0, 1 or 2.

In one particular embodiment, the compound of formula (34) is represented by the structure:

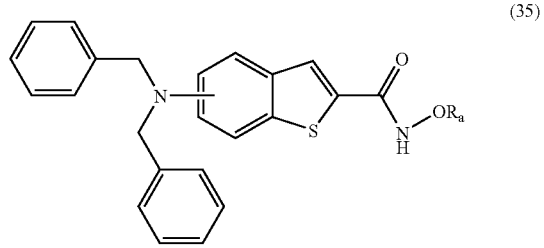
(35)

In another embodiment, the prodrug of the present invention is represented by the structure of formula (36):

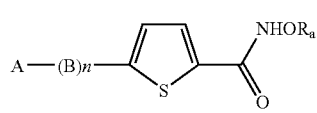
(36)

wherein
A is alkyl, aryl or a group selected from:

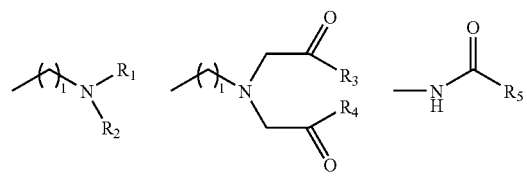

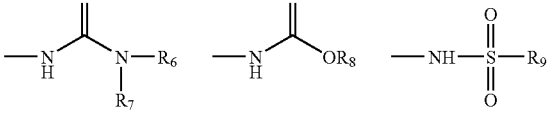

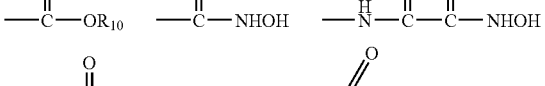

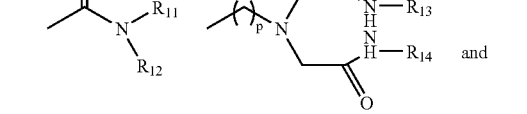

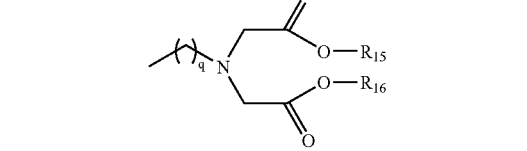

wherein $R_1$-$R_{16}$ are independently of each other a hydrogen or an unsubstituted or substituted alkyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring;

B is

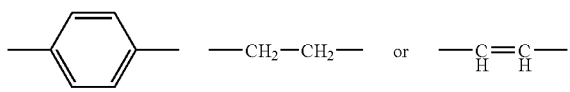

n is 0 or 1; and l, p and q are independently of each other 0, 1 or 2.

As demonstrated herein, the hydroxamic acid derivative prodrugs of the present invention show improved solubility and cellular permeability as compared to the free hydroxamic acid derivatives, and are histone deacetylase (HDAC) inhibitors. Accordingly, in one embodiment, the invention relates to a method of inhibiting the activity of a histone deacetylase comprising contacting the histone deacetylase with an effective amount of one or more of the hydroxamic acid prodrugs described herein. In one embodiment, the prodrugs are converted in-vivo into the free hydroxamic acid that is the active agent. In another embodiment the prodrugs reach the cellular target intact, and are themselves the active agent.

Chemical Definitions

An "aliphatic group" is non-aromatic, consists solely of carbon and hydrogen and can optionally contain one or more units of unsaturation, e.g., double and/or triple bonds. An aliphatic group can be straight chained, branched or cyclic. When straight chained or branched, an aliphatic group typically contains between about 1 and about 12 carbon atoms, more typically between about 1 and about 6 carbon atoms. When cyclic, an aliphatic group typically contains between about 3 and about 10 carbon atoms, more typically between about 3 and about 7 carbon atoms. Aliphatic groups are preferably $C_1$-$C_{12}$ straight chained or branched alkyl groups (i.e., completely saturated aliphatic groups), more preferably $C_1$-$C_6$ straight chained or branched alkyl groups. Examples include methyl, ethyl, n-propyl, iso-propyl, n-butyl, sec-butyl, and tert-butyl.

An "alkenyl group" as used herein includes any group containing one or more double bonds. An "alkynyl group" as used herein includes any group containing one or more triple bonds.

An "aromatic group" (also referred to as an "aryl group") as used herein includes carbocyclic aromatic groups, heterocyclic aromatic groups (also referred to as "heteroaryl"), and fused polycyclic aromatic ring system as defined herein.

A "carbocyclic aromatic group" is an aromatic ring of 5 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g., 1-naphthyl and 2-naphthyl; anthracenyl, e.g., 1-anthracenyl, 2-anthracenyl; phenanthrenyl; fluorenonyl, e.g., 9-fluorenonyl, indanyl and the like. A carbocyclic aromatic group is optionally substituted with a designated number of substituents, described below.

A "heterocyclic aromatic group" (or "heteroaryl") is a monocyclic, bicyclic or tricyclic aromatic ring of 5- to 14-ring atoms of carbon and from one to four heteroatoms selected from O, N, or S. Examples of heteroaryl include, but are not limited to pyridyl, e.g., 2-pyridyl (also referred to as α-pyridyl), 3-pyridyl (also referred to as β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like. Heterocyclic aromatic (or heteroaryl) as defined above may be optionally substituted with a designated number of substituents, as described below for aromatic groups.

A "fused polycyclic aromatic" ring system is a carbocyclic aromatic group or heteroaryl fused with one or more other heteroaryl or nonaromatic heterocyclic ring. Examples include, quinolinyl and isoquinolinyl, e.g., 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g., 2-benzofuranyl and 3-benzofuranyl; dibenzofuranyl, e.g., 2,3-dihydrobenzofuranyl; dibenzothiophenyl; benzothienyl, e.g., 2-benzothienyl and 3-benzothienyl; indolyl, e.g., 2-indolyl and 3-indolyl; benzothiazolyl, e.g., 2-benzothiazolyl; benzooxazolyl, e.g., 2-benzooxazolyl; benzimidazolyl, e.g., 2-benzoimidazolyl; isoindolyl, e.g., 1-isoindolyl and 3-isoindolyl; benzotriazolyl; purinyl; thianaphthenyl, pyrazinyl and the like. Fused polycyclic aromatic ring systems may optionally be substituted with a designated number of substituents, as described herein.

A "heterocyclic ring" (also referred to herein as "heterocyclyl"), is a monocyclic, bicyclic or tricyclic saturated or unsaturated ring of 5- to 14-ring atoms of carbon and from one to four heteroatoms selected from O, N, S or P. Examples of heterocyclic rings include, but are not limited to: pyrrolidinyl, piperidinyl, morpholinyl, thiamorpholinyl, piperazinyl, dihydrofuranyl, tetrahydrofuranyl, dihydropyranyl, tetrahydropyranyl, dihydroquinolinyl, tetrahydroquinolinyl, dihydroisoquinolinyl, tetrahydroisoquinolinyl, dihydropyrazinyl, tetrahydropyrazinyl, dihydropyridyl, tetrahydropyridyl and the like.

Furthermore, a "nitrogen containing heterocyclic ring" is a heterocyclic ring as defined above, which contains at least one nitrogen atom in the ring system. The nitrogen containing heterocyclic ring can comprise nitrogen as the sole ring heteroatom, or can comprise one or more additional heteroatoms such as O, S, N, or P.

A "cycloalkyl group" is a monocyclic, bicyclic, or tricyclic saturated or unsaturated ring of 5- to 14-ring atoms of carbon atoms. Examples of heterocyclic rings include, but are not limited to: cyclopentanyl, cyclopentenyl, cyclohexanyl, and cyclohexenyl and the like.

An "alkylaryl group" (arylalkyl) is an alkyl group substituted with an aromatic group, preferably a phenyl group. A preferred alkylaryl group is a benzyl group. Suitable aromatic groups are described herein and suitable alkyl groups are described herein. Suitable substituents for an alkylaryl group are described herein.

An "alkyheterocyclyl" group" is an alkyl group substituted with a heterocyclyl group. Suitable heterocyclyl groups are described herein and suitable alkyl groups are described herein. Suitable substituents for an alkyheterocyclyl group are described herein.

An "alkycycloalkyl group" is an alkyl group substituted with a cycloalkyl group. Suitable cycloalkyl groups are described herein and suitable alkyl groups are described herein. Suitable substituents for an alkycycloalkyl group are described herein.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy, and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

As used herein, an "arylalkylamino group" is an arylalkyl group that is attached to a compound via a nitrogen on the alkyl portion of the arylalkyl.

An "amino acid protecting group" or "amino protecting group" as used herein refers to any functional group commonly used to protect the α-amino group of an amino acid. Suitable α-amino acid protecting groups Prl, include, but are not limited to, tertiary-butyloxycarbonyl (BOC), isoamyloxycarbonyl (AOC), o-nitrophenylsulfenyl (NPS), fluoroenylmethyloxycarbonyl (FMOC), o-nitropyridinylsulfenyl (NPYS), biphenylproploxycarbonyl (BPOC), or any other known amino protecting group.

A "residue of an amino acid" as used herein refers to any residue of a natural or unnatural amino acid, non-limiting examples of which are residues of alanine, arginine, asparagine, aspartic acid, cysteine, homocysteine, glutamine, glutamic acid, isoleucine, norleucine, glycine, phenylglycine, leucine, histidine, methionine, lysine, phenylalanine, homophenylalanine, ornithine, proline, serine, homoserine, valine, norvaline, threonine, tryptophane, tyrosine, and the like, it being possible for each of the mentioned amino acids (with the exception of glycine or any other amino acid without asymmetric carbon atom) to be in the D-, L- or D,L-form.

As used herein, many moieties or groups are referred to as being either "substituted or unsubstituted". When a moiety is referred to as substituted, it denotes that any portion of the moiety that is known to one skilled in the art as being available for substitution can be substituted. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

Stereochemistry

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the HDAC inhibitors of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. For example, the enantiomeric excess can be about 60% or more, about 70% or more, about 80% or more, about 90% or more, and the like. In a particular embodiment when a specific absolute configuration is designated, the enantiomeric excess of depicted compounds is at least about 90%. In a more particular embodiment, the enantiomeric excess of the compounds is at least about 95%, such as at least about 97.5%, for example, at least 99% enantiomeric excess.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereoisomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

Pharmaceutically Acceptable Salts

The hydroxamic acid prodrugs described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid and the like. Pharmaceutically acceptable salts can also be prepared by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also be salts formed from elemental anions such as chlorine, bromine and iodine.

The preparation of the pharmaceutically acceptable salts described above and other typical pharmaceutically acceptable salts is more fully described by Berg et al., "Pharmaceutical Salts," J. Pharm. Sci., 1977:66:1-19.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in a polymorphic form, in amorphous form, and have any particle size. Furthermore, the compound particles may be micronized, or may be agglomerated, particulate granules, powders, oils, oily suspensions or any other form of solid or liquid physical form.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The invention also relates to methods of using the hydroxamic acid prodrugs described herein. As demonstrated herein, the hydroxamic acid prodrugs of the present invention are useful for the treatment of cancer. In addition, there is a wide range of other diseases for which hydroxamic acid derivatives have been found useful, which the prodrugs of the present invention are also useful for. Non-limiting examples are thioredoxin (TRX)-mediated diseases as described herein, and diseases of the central nervous system (CNS) as described herein.

1. Treatment of Cancer

As demonstrated herein, the hydroxamic acid prodrugs of the present invention are useful for the treatment of cancer. Accordingly, in one embodiment, the invention relates to a method of treating cancer in a subject in need of treatment comprising administering to said subject a therapeutically effective amount of the hydroxamic acid prodrugs described herein.

The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

2. Treatment of Thioredoxin (TRX)-Mediated Diseases

In another embodiment, the hydroxamic acid prodrugs are used in a method of treating a thioredoxin (TRX)-mediated disease or disorder in a subject in need thereof, comprising administering to the subject a therapeutically effective amount of one or more of the hydroxamic acid prodrugs described herein.

Examples of TRX-mediated diseases include, but are not limited to, acute and chronic inflammatory diseases, autoimmune diseases, allergic diseases, diseases associated with oxidative stress, and diseases characterized by cellular hyperproliferation.

Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fascitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemohorragic shock; hyperalgesia: inflammatory bowel disease; multiple sclerosis; myopathies (e.g., muscle protein metabolism, esp. in sepsis); osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes. Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

3. Treatment of Diseases of the Central Nervous System (CNS)

In another embodiment, the hydroxamic acid prodrugs are used in a method of treating a disease of the central nervous system in a subject in need thereof comprising administering to the subject a therapeutically effective amount of any one or more of the hydroxamic acid prodrugs described herein.

In a particular embodiment, the CNS disease is a neurodegenerative disease. In a further embodiment, the neurodegenerative disease is an inherited neurodegenerative disease, such as those inherited neurodegenerative diseases that are polyglutamine expansion diseases. Generally, neurodegenerative diseases can be grouped as follows:

I. Disorders characterized by progressive dementia in the absence of other prominent neurologic signs, such as Alzheimer's disease; Senile dementia of the Alzheimer type; and Pick's disease (lobar atrophy).

II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy).

III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome.

IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders).

V. Syndrome of central autonomic nervous system failure (Shy-Drager syndrome).

VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia.

VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy.

VIII. Syndromes of progressive visual loss such as pigmentary degeneration of the retina (retinitis pigmentosa), and hereditary optic atrophy (Leber's disease).

Definitions

The term "treating" in its various grammatical forms in relation to the present invention refers to preventing (i.e., chemoprevention), curing, reversing, attenuating, alleviating, minimizing, suppressing or halting the deleterious effects of a disease state, disease progression, disease causative agent (e.g., bacteria or viruses) or other abnormal condition. For example, treatment may involve alleviating a symptom (i.e., not necessary all symptoms) of a disease or attenuating the progression of a disease. Because some of the inventive methods involve the physical removal of the etiological agent, the artisan will recognize that they are equally effective in situations where the inventive compound is administered prior to, or simultaneous with, exposure to the etiological agent (prophylactic treatment) and situations where the inventive compounds are administered after (even well after) exposure to the etiological agent.

Treatment of cancer, as used herein, refers to partially or totally inhibiting, delaying or preventing the progression of cancer including cancer metastasis; inhibiting, delaying or preventing the recurrence of cancer including cancer metastasis; or preventing the onset or development of cancer (chemoprevention) in a mammal, for example a human.

As used herein, the term "therapeutically effective amount" is intended to encompass any amount that will achieve the desired therapeutic or biological effect. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

In the present invention, when the prodrugs are used to treat or prevent cancer, the desired biological response is partial or total inhibition, delay or prevention of the progression of cancer including cancer metastasis; inhibition, delay or prevention of the recurrence of cancer including cancer metastasis; or the prevention of the onset or development of cancer (chemoprevention) in a mammal, for example a human.

Furthermore, in the present invention, when the prodrugs are used to treat and/or prevent thioredoxin (TRX)-mediated diseases and conditions, a therapeutically effective amount is an amount that regulates, for example, increases, decreases or maintains a physiologically suitable level of TRX in the subject in need of treatment to elicit the desired therapeutic effect. The therapeutic effect is dependent upon the specific TRX-mediated disease or condition being treated. As such, the therapeutic effect can be a decrease in the severity of symptoms associated with the disease or disorder and/or inhibition (partial or complete) of progression of the disease or disorder.

Furthermore, in the present invention, when the prodrugs are used to treat and/or prevent diseases or disorders of the central nervous system (CNS), a therapeutically effective amount is dependent upon the specific disease or disorder being treated. As such, the therapeutic effect can be a decrease in the severity of symptoms associated with the disease or disorder and/or inhibition (partial or complete) of progression of the disease or disorder.

In addition, a therapeutically effective amount can be an amount that inhibits histone deacetylase.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

Histone Deacetylases and Histone Deacetylase Inhibitors

As demonstrated herein, the hydroxamic acid prodrugs of the present invention are histone deacetylase (HDAC) inhibitors. Accordingly, in one embodiment, the invention relates to a method of inhibiting the activity of histone deacetylase comprising contacting the histone deacetylase with an effective amount of one or more of the hydroxamic acid prodrugs described herein.

In one embodiment, the hydroxamic acid prodrugs are potent inhibitors of Class I histone deacetylases (Class I HDACs). Class I HDACs include histone deacetylase 1 (HDAC-1), histone deacetylase 2 (HDAC-2), histone deacetylase 3 (HDAC-3) and histone deacetylase 8 (HDAC-8). In a particular embodiment, the hydroxamic acid prodrugs are potent inhibitors of histone deacetylase 1 (HDAC-1). In another embodiment, the hydroxamic acid prodrugs are potent inhibitors of Class II histone deacetylases (Class II HDACs). Class II HDACs include histone deacetylase 4 (HDAC-4), histone deacetylase 5 (HDAC-8), histone deacetylase 6 (HDAC-6), histone deacetylase 7 (HDAC-7) and histone deacetylase 9 (HDAC-9).

"Histone deacetylases (HDACs)," as that term is used herein, are enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA) induce growth arrest, differentiation and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of NAD dependent enzymes that are related to the yeast SIR2 proteins and are not inhibited by hydroxamic acid-based HDAC inhibitors.

"Histone deacetylase inhibitors" or "HDAC inhibitors," as that term is used herein are compounds that are capable of inhibiting the deacetylation of histones in vivo, in vitro or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures that can assay for the accumulation of acetylated histones can be used to determine the HDAC inhibitory activity of compounds of interest. It is understood that compounds that can inhibit histone deacetylase activity can also bind to other substrates and as such can inhibit other biologically active molecules such as enzymes.

For example, in patients receiving HDAC inhibitors, the accumulation of acetylated histones in peripheral mononuclear cells as well as in tissue treated with HDAC inhibitors can be determined against a suitable control.

HDAC inhibitory activity of a particular compound can be determined in vitro using, for example, an enzymatic assay which shows inhibition of at least one histone deacetylase. Further, determination of the accumulation of acetylated histones in cells treated with a particular composition can be determinative of the HDAC inhibitory activity of a compound.

Assays for the accumulation of acetylated histones are well known in the literature. See, for example, Marks, P. A. et al., J. Natl. Cancer Inst., 92:1210-1215, 2000, Butler, L. M. et al., Cancer Res. 60:5165-5170 (2000), Richon, V. M. et al., Proc. Natl. Acad. Sci., USA, 95:3003-3007, 1998, and Yoshida, M. et al., J. Biol. Chem., 265:17174-17179, 1990.

For example, an enzymatic assay to determine the activity of an HDAC inhibitor compound can be conducted as follows. Briefly, the effect of an HDAC inhibitor compound on affinity purified human epitope-tagged (Flag) HDAC1 can be assayed by incubating the enzyme preparation in the absence of substrate on ice for about 20 minutes with the indicated amount of inhibitor compound. Substrate ([$^3$H]acetyl-labelled murine erythroleukemia cell-derived histone) can be added and the sample can be incubated for 20 minutes at 37° C. in a total volume of 30 μL. The reaction can then be stopped and released acetate can be extracted and the amount of radioactivity release determined by scintillation counting. An alternative assay useful for determining the activity of an HDAC inhibitor compound is the "HDAC Fluorescent Activity Assay; Drug Discovery Kit-AK-500" available from BIO-MOL® Research Laboratories, Inc., Plymouth Meeting, Pa.

In vivo studies can be conducted as follows. Animals, for example, mice, can be injected intraperitoneally with an HDAC inhibitor compound. Selected tissues, for example, brain, spleen, liver etc, can be isolated at predetermined times, post administration. Histones can be isolated from tissues essentially as described by Yoshida et al., J. Biol. Chem. 265:17174-17179, 1990. Equal amounts of histones (about 1 µg) can be electrophoresed on 15% SDS-polyacrylamide gels and can be transferred to Hybond-P filters (available from Amersham). Filters can be blocked with 3% milk and can be probed with a rabbit purified polyclonal anti-acetylated histone H4 antibody (αAc-H4) and anti-acetylated histone H3 antibody (αAc-H3) (Upstate Biotechnology, Inc.). Levels of acetylated histone can be visualized using a horseradish peroxidase-conjugated goat anti-rabbit antibody (1:5000) and the SuperSignal chemiluminescent substrate (Pierce). As a loading control for the histone protein, parallel gels can be run and stained with Coomassie Blue (CB).

In addition, hydroxamic acid-based HDAC inhibitors have been shown to up regulate the expression of the $p21^{WAF1}$ gene. The $p21^{WAF1}$ protein is induced within 2 hours of culture with HDAC inhibitors in a variety of transformed cells using standard methods. The induction of the $p21^{WAF1}$ gene is associated with accumulation of acetylated histones in the chromatin region of this gene. Induction of $p21^{WAF1}$ can therefore be recognized as involved in the G1 cell cycle arrest caused by HDAC inhibitors in transformed cells.

Typically, HDAC inhibitors fall into five general classes: 1) hydroxamic acid derivatives; 2) Short-Chain Fatty Acids (SCFAs); 3) cyclic tetrapeptides; 4) benzamides; and 5) electrophilic ketones. Examples of such HDAC inhibitors are set forth below.

A. Hydroxamic Acid Derivatives such as suberoylanilide hydroxamic acid (SAHA) (Richon et al., Proc. Natl. Acad. Sci. USA 95, 3003-3007 (1998)); m-carboxycinnamic acid bishydroxamide (CBHA) (Richon et al., supra); pyroxamide; trichostatin analogues such as trichostatin A (TSA) and trichostatin C (Koghe et al. 1998. Biochem. Pharmacol. 56: 1359-1364); salicylhydroxamic acid (Andrews et al., International J. Parasitology 30, 761-768 (2000)); suberoyl bishydroxamic acid (SBHA) (U.S. Pat. No. 5,608,108); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); 6-(3-chlorophenylureido) carpoic hydroxamic acid (3Cl-UCHA); oxamflatin [(2E)-5-[3-[(phenylsulfonyl)amino]phenyl]-pent-2-en-4-ynohydroxamic acid] (Kim et al. Oncogene, 18: 2461 2470 (1999)); A-161906, Scriptaid (Su et al. 2000 Cancer Research, 60: 3137-3142); PXD-101 (Prolifix); LAQ-824; CHAP; MW2796 (Andrews et al., supra); MW2996 (Andrews et al., supra); or any of the hydroxamic acids disclosed in U.S. Pat. Nos. 5,369,108, 5,932,616, 5,700,811, 6,087,367 and 6,511,990.

"Hydroxamic acid derivative histone deactylase inhibitor," as used herein, refers to the class of histone deactylase inhibitors that are hydroxamic acid derivatives. Examples of these compounds are provided above.

"A residue of a hydroxamic acid derivative histone deactylase inhibitor" refers to the entire portion of the hydroxamic acid derivative histone deactylase inhibitor excluding the hydroxamic acid moiety.

B. Cyclic Tetrapeptides such as trapoxin A (TPX)-cyclic tetrapeptide (cyclo-(L-phenylalanyl-L-phenylalanyl-D-pipecolinyl-L-2-amino-8-oxo-9,10-epoxy decanoyl)) (Kijima et al., J. Biol. Chem. 268, 22429-22435 (1993)); FR901228 (FK 228, depsipeptide) (Nakajima et al., Ex. Cell Res. 241, 126-133 (1998)); FR225497 cyclic tetrapeptide (H. Mori et al., PCT Application WO 00/08048 (17 Feb. 2000)); apicidin cyclic tetrapeptide [cyclo(N—O-methyl-L-tryptophanyl-L-isoleucinyl-D-pipecolinyl-L-2-amino-8-oxodecanoyl)] (Darkin-Rattray et al., Proc. Natl. Acad. Sci. USA 93, 1314313147 (1996)); apicidin Ia, apicidin Ib, apicidin Ic, apicidin IIa, and apicidin IIb (P. Dulski et al., PCT Application WO 97/11366); CHAP, HC-toxin cyclic tetrapeptide (Bosch et al., Plant Cell 7, 1941-1950 (1995)); WF27082 cyclic tetrapeptide (PCT Application WO 98/48825); and chlamydocin (Bosch et al., supra).

C. Short chain fatty acid (SCFA) derivatives such as: sodium butyrate (Cousens et al., J. Biol. Chem. 254, 1716-1723 (1979)); isovalerate (McBain et al., Biochem. Pharm. 53: 1357-1368 (1997)); valerate (McBain et al., supra); 4-phenylbutyrate (4-PBA) (Lea and Tulsyan, Anticancer Research, 15, 879-873 (1995)); phenylbutyrate (PB) (Wang et al., Cancer Research, 59, 2766-2799 (1999)); propionate (McBain et al., supra); butyramide (Lea and Tulsyan, supra); isobutyramide (Lea and Tulsyan, supra); phenylacetate (Lea and Tulsyan, supra); 3-bromopropionate (Lea and Tulsyan, supra); tributyrin (Guan et al., Cancer Research, 60, 749-755 (2000)); valproic acid, valproate and Pivanex™.

D. Benzamide derivatives such as CI-994; MS-275 [N-(2-aminophenyl)-4-[N-(pyridin-3-yl methoxycarbonyl)aminomethyl]benzamide] (Saito et al., Proc. Natl. Acad. Sci. USA 96, 4592-4597 (1999)); and 3'-amino derivative of MS-275 (Saito et al., supra).

E. Electrophilic ketone derivatives such as trifluoromethyl ketones (Frey et al, Bioorganic & Med. Chem. Lett. (2002), 12, 3443-3447; U.S. Pat. No. 6,511,990) and α-keto amides such as N-methyl-α-ketoamides F. Other HDAC Inhibitors such as natural products, psammaplins, and Depudecin (Kwon et al. 1998. PNAS 95: 3356-3361).

Combination Therapy

The hydroxamic acid prodrugs of the present invention can be administered alone or in combination with other therapies suitable for the disease or disorder being treated. Where separate dosage formulations are used, the hydroxamic acid prodrug and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the hydroxamic acid prodrug and the other therapeutic agent are realized by the patient at substantially the same time. Such beneficial effect is preferably achieved when the target blood level concentrations of each active drug are maintained at substantially the same time.

The hydroxamic acid prodrugs can be administered in combination with any one or more of an HDAC inhibitor, an alkylating agent, an antibiotic agent, an antimetabolic agent, a hormonal agent, a plant-derived agent, an anti-angiogenic agent, a differentiation inducing agent, a cell growth arrest inducing agent, an apoptosis inducing agent, a cytotoxic agent, a biologic agent, a gene therapy agent, or any combination thereof.

Alkylating Agents

Alkylating agents react with nucleophilic residues, such as the chemical entities on the nucleotide precursors for DNA production. They affect the process of cell division by alkylating these nucleotides and preventing their assembly into DNA.

Examples of alkylating agents include, but are not limited to, bischloroethylamines (nitrogen mustards, e.g., chlorambucil, cyclophosphamide, ifosfamide, mechlorethamine, melphalan, uracil mustard), aziridines (e.g., thiotepa), alkyl alkone sulfonates (e.g., busulfan), nitrosoureas (e.g., carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups.

Under physiological conditions, these drugs ionize and produce positively charged ion that attach to susceptible nucleic acids and proteins, leading to cell cycle arrest and/or cell death. The alkylating agents are cell cycle phase nonspecific agents because they exert their activity independently of the specific phase of the cell cycle. The nitrogen mustards and alkyl alkone sulfonates are most effective against cells in the G1 or M phase. Nitrosoureas, nitrogen mustards, and aziridines impair progression from the G1 and S phases to the M phases. Chabner and Collins eds. (1990) "Cancer Chemotherapy: Principles and Practice", Philadelphia: JB Lippincott.

The alkylating agents are active against wide variety of neoplastic diseases, with significant activity in the treatment of leukemias and lymphomas as well as solid tumors. Clinically this group of drugs is routinely used in the treatment of acute and chronic leukemias; Hodgkin's disease; non-Hodgkin's lymphoma; multiple myeloma; primary brain tumors; carcinomas of the breast, ovaries, testes, lungs, bladder, cervix, head and neck, and malignant melanoma.

Antibiotics

Antibiotics (e.g., cytotoxic antibiotics) act by directly inhibiting DNA or RNA synthesis and are effective throughout the cell cycle. Examples of antibiotic agents include anthracyclines (e.g., doxorubicin, daunorubicin, epirubicin, idarubicin and anthracenedione), mitomycin C, bleomycin, dactinomycin, and plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions.

Bleomycin is generally believed to chelate iron and forms an activated complex, which then binds to bases of DNA, causing strand scissions and cell death.

The antibiotic agents have been used as therapeutics across a range of neoplastic diseases, including carcinomas of the breast, lung, stomach and thyroids, lymphomas, myelogenous leukemias, myelomas, and sarcomas.

Antimetabolic Agents

Antimetabolic agents (i.e., antimetabolites) are a group of drugs that interfere with metabolic processes vital to the physiology and proliferation of cancer cells. Actively proliferating cancer cells require continuous synthesis of large quantities of nucleic acids, proteins, lipids, and other vital cellular constituents.

Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Antimetabolic agents have widely used to treat several common forms of cancer including carcinomas of colon, rectum, breast, liver, stomach and pancreas, malignant melanoma, acute and chronic leukemia and hair cell leukemia.

Hormonal Agents

The hormonal agents are a group of drug that regulate the growth and development of their target organs. Most of the hormonal agents are sex steroids and their derivatives and analogs thereof, such as estrogens, progestogens, anti-estrogens, androgens, antiandrogens and progestins. These hormonal agents may serve as antagonists of receptors for the sex steroids to down regulate receptor expression and transcription of vital genes. Examples of such hormonal agents are synthetic estrogens (e.g., diethylstibestrol), antiestrogens (e.g., tamoxifen, toremifene, fluoxymesterol and raloxifene), antiandrogens (e.g., bicalutamide, nilutamide, flutamide), aromatase inhibitors (e.g., aminoglutethimide, anastrozole and tetrazole), and luteinizing hormone release hormone (LHRH) analogues (e.g., ketoconazole, goserelin acetate, leuprolide, megestrol acetate and mifepristone).

Hormonal agents are used to treat breast cancer, prostate cancer, melanoma, and meningioma. Because the major action of hormones is mediated through steroid receptors, 60% receptor-positive breast cancer responded to first-line hormonal therapy; and less than 10% of receptor-negative tumors responded. Specifically, progestogens are used to treat endometrial cancers, since these cancers occur in women that are exposed to high levels of oestrogen unopposed by progestogen. Antiandrogens are used primarily for the treatment of prostate cancer, which is hormone dependent. They are used to decrease levels of testosterone, and thereby inhibit growth of the tumor.

Hormonal treatment of breast cancer involves reducing the level of oestrogen-dependent activation of oestrogen receptors in neoplastic breast cells. Anti-oestrogens act by binding to oestrogen receptors and prevent the recruitment of coactivators, thus inhibiting the oestrogen signal.

LHRH analogues are used in the treatment of prostate cancer to decrease levels of testosterone and so decrease the growth of the tumor.

Aromatase inhibitors act by inhibiting the enzyme required for hormone synthesis. In post-menopausal women, the main source of oestrogen is through the conversion of androstenedione by aromatase.

Plant-Derived Agents

Plant-derived agents are a group of drugs that are derived from plants or modified based on the molecular structure of the agents. They inhibit cell replication by preventing the assembly of the cell's components that are essential to cell division.

Examples of plant derived agents include vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission.

Plant-derived agents are used to treat many forms of cancer. For example, vincristine is used in the treatment of the leukemias, Hodgkin's and non-Hodgkin's lymphoma, and the childhood tumors neuroblastoma, rhabdomyosarcoma, and Wilm's tumor. Vinblastine is used against the lymphomas, testicular cancer, renal cell carcinoma, mycosis fungoides, and Kaposi's sarcoma. Docetaxel has shown promising activity against advanced breast cancer, non-small cell lung cancer (NSCLC), and ovarian cancer.

Etoposide is active against a wide range of neoplasms, of which small cell lung cancer, testicular cancer, and NSCLC are most responsive.

Biologic Agents

Biologic agents are a group of biomolecules that elicit cancer/tumor regression when used alone or in combination with chemotherapy and/or radiotherapy. Examples of biologic agents include immuno-modulating proteins such as cytokines, monoclonal antibodies against tumor antigens, tumor suppressor genes, and cancer vaccines.

Cytokines possess profound immunomodulatory activity. Some cytokines such as interleukin-2 (IL-2, aldesleukin) and interferon-a (IFN-a) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself.

Interferon-α includes more than 23 related subtypes with overlapping activities. IFN-α has demonstrated activity against many solid and hematologic malignancies, the later appearing to be particularly sensitive.

Examples of interferons include, interferon-α, interferon-β (fibroblast interferon), and interferon-γ (fibroblast interferon). Examples of other cytokines include erythropoietin (epoietin-α), granulocyte-CSF (filgrastin), and granulocyte, macrophage-CSF (sargramostim). Other immunomodulating agents other than cytokines include bacillus Calmette-Guerin, levamisole, and octreotide, a long-acting octapeptide that mimics the effects of the naturally occurring hormone somatostatin.

Furthermore, the anti-cancer treatment can comprise treatment by immunotherapy with antibodies and reagents used in tumor vaccination approaches. The primary drugs in this therapy class are antibodies, alone or carrying compounds such as toxins or chemotherapeutics/cytotoxics to cancer cells. Monoclonal antibodies against tumor antigens are antibodies elicited against antigens expressed by tumors, preferably tumor-specific antigens. For example, monoclonal antibody HERCEPTIN® (trastuzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein.

Another example of monoclonal antibodies against tumor antigens is RITUXAN® (rituximab) that is raised against CD20 on lymphoma cells and selectively deplete normal and malignant CD20+ pre-B and mature B cells.

RITUXAN is used as single agent for the treatment of patients with relapsed or refractory low-grade or follicular, CD20+, B cell non-Hodgkin's lymphoma. MYELOTARG® (gemtuzumab ozogamicin) and CAMPATH® (alemtuzumab) are further examples of monoclonal antibodies against tumor antigens that may be used.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle checkpoints and resulting in a higher rate of controlled cell growth-cancer. Examples of the tumor suppressor genes include Duc-4, NF-1, NF-2, RB, p53, WT1, BRCA1, and BRCA2.

DPC4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WTI is involved in Wilm's tumor of the kidneys. BRCA1 is involved in breast and ovarian cancer, and BRCA2 is involved in breast cancer. The tumor suppressor gene can be transferred into the tumor cells where it exerts its tumor suppressing functions.

Cancer vaccines are a group of agents that induce the body's specific immune response to tumors. Most of cancer vaccines under research and development and clinical trials are tumor-associated antigens (TAAs). TAAs are structures (i.e., proteins, enzymes or carbohydrates) that are present on tumor cells and relatively absent or diminished on normal cells. By virtue of being fairly unique to the tumor cell, TAAs provide targets for the immune system to recognize and cause their destruction. Examples of TAAs include gangliosides (GM2), prostate specific antigen (PSA), α-fetoprotein (AFP), carcinoembryonic antigen (CEA) (produced by colon cancers and other adenocarcinomas, e.g., breast, lung, gastric, and pancreatic cancers), melanoma-associated antigens (MART-1, gap100, MAGE 1,3 tyrosinase), papillomavirus E6 and E7 fragments, whole cells or portions/lysates of autologous tumor cells and allogeneic tumor cells.

Other Therapies

Recent developments have introduced, in addition to the traditional cytotoxic and hormonal therapies used to treat cancer, additional therapies for the treatment of cancer.

For example, many forms of gene therapy are undergoing preclinical or clinical trials.

In addition, approaches are currently under development that are based on the inhibition of tumor vascularization (angiogenesis). The aim of this concept is to cut off the tumor from nutrition and oxygen supply provided by a newly built tumor vascular system.

In addition, cancer therapy is also being attempted by the induction of terminal differentiation of the neoplastic cells. Suitable differentiation agents include the compounds disclosed in any one or more of the following references, the contents of which are incorporated by reference herein.

a) Polar compounds (Marks et al (1987); Friend, C., Scher, W., Holland, J. W., and Sato, T. (1971) Proc. Natl. Acad. Sci. (USA) 68: 378-382; Tanaka, M., Levy, J., Terada, M., Breslow, R., Rifkind, R. A., and Marks, P. A. (1975) Proc. Natl. Acad. Sci. (USA) 72: 1003-1006; Reuben, R. C., Wife, R. L., Breslow, R., Rifkind, R. A., and Marks, P. A. (1976) Proc. Natl. Acad. Sci. (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) Proc. Natl. Acad. Sci. (USA) 78: 4990-4994; Schwartz, E. L., Snoddy, J. R., Kreutter, D., Rasmussen, H., and Sartorelli, A. C. (1983) Proc. Am. Assoc. Cancer Res. 24: 18; Tanenaga, K., Hozumi, M., and Sakagami, Y. (1980) Cancer Res. 40: 914-919);

c) Steroid hormones (Lotem, J. and Sachs, L. (1975) Int. J. Cancer 15: 731-740);

d) Growth factors (Sachs, L. (1978) Nature (Lond.) 274: 535, Metcalf, D. (1985) Science, 229: 16-22);

e) Proteases (Scher, W., Scher, B. M., and Waxman, S. (1983) Exp. Hematol. 11: 490-498; Scher, W., Scher, B. M., and Waxman, S. (1982) Biochem. & Biophys Res. Comm. 109: 348-354);

f) Tumor promoters (Huberman, E. and Callaham, M. F. (1979) Proc. Natl. Acad. Sci. (USA) 76: 1293-1297; Lottem, J. and Sachs, L. (1979) Proc. Natl. Acad. Sci. (USA) 76: 5158-5162); and g) inhibitors of DNA or RNA synthesis (Schwartz, E. L. and Sartorelli, A. C. (1982) Cancer Res. 42: 2651-2655, Terada, M., Epner, E., Nudel, U., Salmon, J., Fibach, E., Rifkind, R. A., and Marks, P. A. (1978) Proc. Natl. Acad. Sci. (USA) 75: 2795-2799; Morin, M. J. and Sartorelli, A. C. (1984) Cancer Res. 44: 2807-2812; Schwartz, E. L., Brown, B. J., Nierenberg, M., Marsh, J. C., and Sartorelli, A. C.

(1983) Cancer Res. 43: 2725-2730; Sugano, H., Furusawa, M., Kawaguchi, T., and Ikawa, Y. (1973) Bibl. Hematol. 39: 943-954; Ebert, P. S., Wars, I., and Buell, D. N. (1976) Cancer Res. 36: 1809-1813; Hayashi, M., Okabe, J., and Hozumi, M. (1979) Gann 70: 235-238).

The use of all of these approaches in combination with the hydroxamic acid prodrugs described herein is within the scope of the present invention.

Dosages and Dosing Schedules

The dosage regimen utilizing the hydroxamic acid prodrugs of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

For oral administration, suitable daily dosages are for example between about 5-4000 mg/m$^2$ administered orally once-daily, twice-daily or three times-daily, continuous (every day) or intermittently (e.g., 3-5 days a week). For example, when used to treat the desired disease, the dose of the hydroxamic acid prodrug can range between about 2 mg to about 2000 mg per day.

The hydroxamic acid prodrug is administered once daily (QD), or divided into multiple daily doses such as twice daily (BID), and three times daily (TID). For administration once a day, a suitably prepared medicament would therefore contain all of the needed daily dose. For administration twice a day, a suitably prepared medicament would therefore contain half of the needed daily dose. For administration three times a day, a suitably prepared medicament would therefore contain one third of the needed daily dose.

In addition, the administration can be continuous, i.e., every day, or intermittently. The terms "intermittent" or "intermittently" as used herein means stopping and starting at either regular or irregular intervals. For example, intermittent administration of an HDAC inhibitor may be administration one to six days per week or it may mean administration in cycles (e.g., daily administration for two to eight consecutive weeks, then a rest period with no administration for up to one week) or it may mean administration on alternate days.

Typically, an intravenous formulation may be prepared which contains a concentration of the hydroxamic acid prodrug of between about 1.0 mg/mL to about 10 mg/mL. In one example, a sufficient volume of intravenous formulation can be administered to a patient in a day such that the total dose for the day is between about 10 and about 1500 mg/m$^2$.

Subcutaneous formulations, preferably prepared according to procedures well known in the art at a pH in the range between about 5 and about 12, also include suitable buffers and isotonicity agents, as described below. They can be formulated to deliver a daily dose of HDAC inhibitor in one or more daily subcutaneous administrations, e.g., one, two, or three times each day.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

It should be apparent to a person skilled in the art that the various modes of administration, dosages and dosing schedules described herein merely set forth specific embodiments and should not be construed as limiting the broad scope of the invention. Any permutations, variations, and combinations of the dosages and dosing schedules are included within the scope of the present invention.

Pharmaceutical Compositions

The prodrugs of the invention, and derivatives, fragments, analogs, homologs pharmaceutically acceptable salts or hydrates thereof, can be incorporated into pharmaceutical compositions suitable for oral administration, together with a pharmaceutically acceptable carrier or excipient. Such compositions typically comprise a therapeutically effective amount of any of the compounds above, and a pharmaceutically acceptable carrier. Preferably, the effective amount is an amount effective to selectively induce terminal differentiation of suitable neoplastic cells and less than an amount which causes toxicity in a patient.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, and the like. Suitable liquid oral formulations include solutions, suspensions, dispersions, emulsions, oils, and the like. In one embodiment of the present invention, the composition is formulated in a capsule. In accordance with this embodiment, the compositions of the present invention comprise in addition to the hydroxamic acid prodrug and the inert carrier or diluent, a hard gelatin capsule.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

For liquid formulations, pharmaceutically acceptable carriers may be aqueous or non-aqueous solutions, suspensions, emulsions, or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the prodrugs are prepared with carriers that will protect the prodrug against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The prodrugs of the present invention may be administered intravenously on the first day of treatment, with oral administration on the second day and all consecutive days thereafter.

The prodrugs of the present invention may be administered for the purpose of preventing disease progression or stabilizing tumor growth.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the prodrug administered to the patient is less than an amount that would cause toxicity in the patient. In the certain embodiments, the amount of the prodrug that is administered to the patient is less than the amount that causes a concentration of the prodrug in the patient's plasma to equal or exceed the toxic level of the prodrug. Preferably, the concentration of the prodrug in the patient's plasma is maintained at about 10 nM. In another embodiment, the concentration of the prodrug in the patient's plasma is maintained at about 25 nM. In another embodiment, the concentration of the prodrug in the patient's plasma is maintained at about 50 nM. In another embodiment, the concentration of the prodrug in the patient's plasma is maintained at about 100 nM. In another embodiment, the concentration of the prodrug in the patient's plasma is maintained at about 500 nM. In another embodiment, the concentration of the prodrug in the patient's plasma is maintained at about 1000 nM. In another embodiment, the concentration of the prodrug in the patient's plasma is maintained at about 2500 nM. In another embodiment, the concentration of the prodrug in the patient's plasma is maintained at about 5000 nM. It has been found with HMBA that administration of the compound in an amount from about 5 gm/m$^2$/day to about 30 gm/m$^2$/day, particularly about 20 gm/m$^2$/day, is effective without producing toxicity in the patient. The optimal amount of the prodrug that should be administered to the patient in the practice of the present invention will depend on the particular compound used and the type of cancer being treated.

In Vitro Methods

The present invention also provides methods of using the hydroxamic acid prodrugs of the present invention for inducing terminal differentiation, cell growth arrest, and/or apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the hydroxamic acid prodrugs described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the hydroxamic acid prodrugs described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the hydroxamic acid prodrugs described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the hydroxamic acid prodrugs described herein.

In another embodiment, the invention relates to an in vitro method of inducing terminal differentiation of tumor cells in a tumor comprising contacting the cells with an effective amount of any one or more of the hydroxamic acid prodrugs described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting HDAC will comprise contacting the cells in vivo, i.e., by administering the prodrugs to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the hydroxamic acid prodrugs described herein.

In a particular embodiment, the present invention relates to a method of selectively inducing terminal differentiation of neoplastic cells and thereby inhibiting proliferation of such cells in a subject. The method comprises administering to the subject an effective amount of one or more of the hydroxamic acid prodrugs described herein.

In another embodiment, the invention relates to a method of selectively inducing cell growth arrest of neoplastic cells and thereby inhibiting proliferation of such cells in a subject. The method comprises administering to the subject an effective amount of one or more of the hydroxamic acid prodrugs described herein.

In another embodiment, the invention relates to a method of selectively inducing apoptosis of neoplastic cells and thereby inhibiting proliferation of such cells in a subject. The method comprises administering to the subject an effective amount of one or more of the hydroxamic acid prodrugs described herein.

In another embodiment, the invention relates to a method of treating a patient having a tumor characterized by proliferation of neoplastic cells. The method comprises administering to the patient one or more of the hydroxamic acid prodrugs described herein. The amount of prodrug is effective to selectively induce terminal differentiation, induce cell growth arrest and/or induce apoptosis of such neoplastic cells and thereby inhibit their proliferation.

The invention is illustrated in the examples in the Experimental Details Section that follows. This section is set forth to aid in an understanding of the invention but is not intended to, and should not be construed to limit in any way the invention as set forth in the claims which follow thereafter.

EXPERIMENTAL DETAILS SECTION

Example 1

Synthesis

The compounds of the present invention were prepared by the general methods outlined in the synthetic schemes below, as exemplified below.

SAHA was acylated using three different procedures:

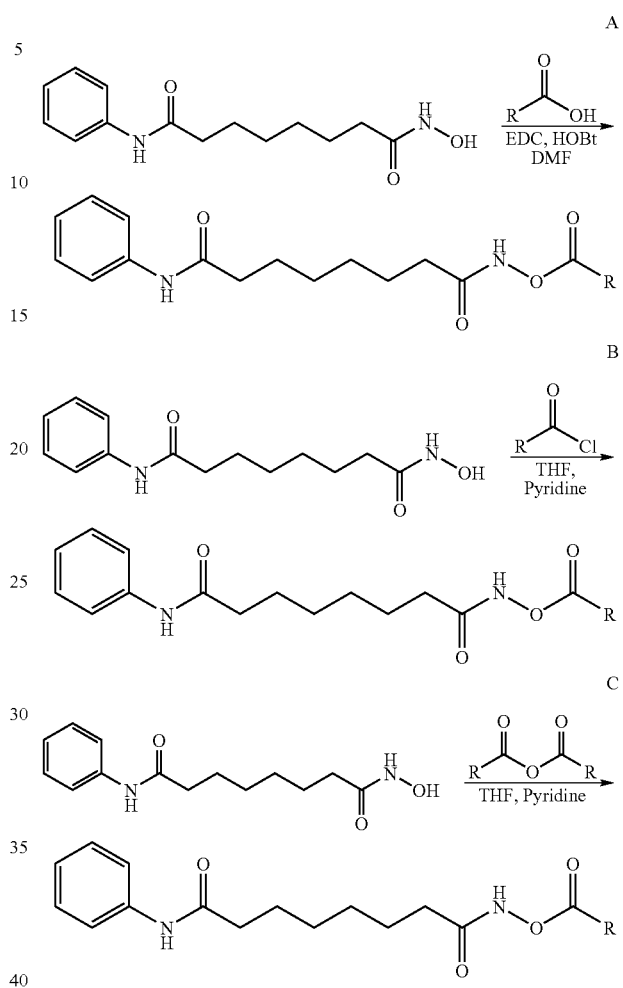

Method A:

Suberoylanilide hydroxamic acid (SAHA, 100 mg) was dissolved in 2 mL of anhydrous DMF. A carboxylic acid (1.5 eq.) was added, followed by HOBt (1 eq.) and EDC (1.5 eq.). The solution was stirred at room temperature overnight. The solvent was removed under reduced pressure and the residue treated with water (5 mL) and EtOAc (2 mL). If a solid formed, the product was collected by filtration after trituration. If no precipitate formed, the aqueous phase was extracted with ethyl acetate (2×10 mL), the organic phase was dried, the solvent removed, and the residue purified by column chromatography (silica, hexanes: EtOAc).

Method B:

Suberoylanilide hydroxamic acid (SAHA, 100 mg) was suspended in 2 mL of anhydrous THF and 1 mL of anhydrous pyridene. An acyl chloride (1.1-1.2 eq.) was added, and the solution was stirred at room temperature overnight. The solvent was reduced to 1 mL water (5 mL) was added. The product precipitated out of solution. It was washed with water and triturated with ethyl acetate to remove any double-acylation byproduct. It was collected by filtration as a white solid.

Method C:

The same procedure as in method B was followed, using an anhydride instead of a chloride as an acylating agent.

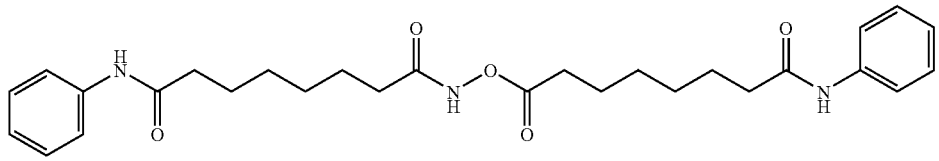

Octanedioic acid phenylamide(7-phenylcarbamoyl-heptanoyloxy)-amide. To a stirring solution of suberanilic acid (3.0 g, 12.0 mmol) in DMF (60 mL) was added 1-hydroxybenzotriazole (1.79 g, 13.2 mmol), 1-(3-dimethylaminopropyl)-3-ethylcarbodiimide hydrochloride (EDCI) (2.54 g, 13.2 mmol). After 5 mins, a solution of SAHA (3.18 g, 12.0 mmol) in DMF (30 mL) was added to the mixture with stirring. After 24 h, the solvent was removed and the residue was triturated with EtOAc (50 mL). The slurry was filtered to yield an off-white solid, which was triturated in $CH_2Cl_2$ (50 mL). The slurry was filtered yielding a white solid (4.6 g, 77%). Half of the material was purified further by repeating the washing procedures with an addition of $H_2O$ (20 mL) in the EtOAc wash. The white solid was filtered to yield the desired material (2.1 g). MP: 151-153° C. $^1$H NMR (DMSO-$d_6$) δ 11.51 (s, 1H), 9.82 (s, 2H), 7.54 (d, J=7.9 Hz, 4H), 7.23 (dd, J=7.9, 7.6 Hz, 4H), 6.97 (t, J=7.6 Hz, 2H), 2.39 (t, J=7.2 Hz, 2H), 2.24 (t, J=6.8 Hz, 4H), 1.98 (t, J=6.8 Hz, 2H), 1.66-1.38 (m, 8H), 1.38-1.16 (m, 8H). $^{13}$C NMR (DMSO-$d_6$) δ 171.33, 169.94, 139.49, 128.72, 123.02, 119.21, 36.49, 32.02, 31.06, 28.50, 28.37, 28.14, 25.12, 25.05, 24.79, 24.38. MS (EI): cal'd (MH$^+$) 496, exp (MH$^+$) 496.

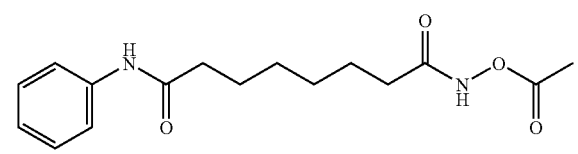

Octanedioic acid acetoxy-amide phenylamide. To a stirring solution of SAHA (0.43 g, 16.3 mmol) in pyridine/$CH_2Cl_2$ (5/5 mL) was added acetic anhydride 1-hydroxybenzotriazole (153 μL, 16.3 mmol). After stirring for 18 h at RT, the solvent was removed, and the material was without further purification. $^1$H NMR (DMSO-$d_6$) δ 11.71 (br s, 1H), 10.01 (br s, 1H), 7.75 (d, J=7.6 Hz, 2H), 7.44 (dd, J=7.6, 7.4 Hz, 2H), 7.17 (t, J=7.4 Hz, 1H), 2.43 (t, J=7.2 Hz, 2H), 2.35-2.20 (m, 2H), 2.30 (s, 3H), 1.82-1.58 (m, 4H), 1.58-1.36 (m, 4H). MS (EI): cal'd (MH$^+$) 307.1, exp (MH$^+$) 307.2.

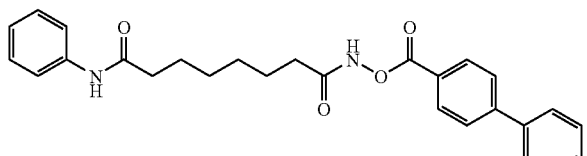

Octanedioic acid (biphenyl-4-carbonyloxy)-amide phenylamide. $^1$H NMR (DMSO-$d_6$) δ 11.85 (br s, 1H), 9.84 (s, 1H), 8.09 (d, J=8.2 Hz, 2H), 7.88 (d, J=8.4 Hz, 2H), 7.76 (d, J=6.6 Hz, 2H), 7.60-7.44 (m, 5H), 7.27 (t, J=7.2 Hz, 2H), 7.00 (t, J=7.4 Hz, 1H), 2.30 (t, J=7.6 Hz, 2H), 2.20 (t, J=7.6 Hz, 2H), 1.70-1.48 (m, 4H), 1.48-1.20 (m, 4H). MS (EI): cal'd (MH$^+$) 445.2, exp (MH$^+$) 445.2.

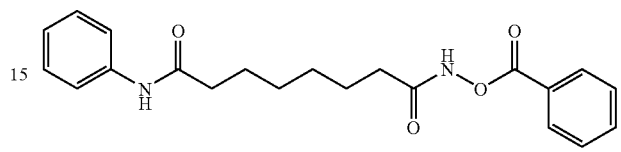

Octanedioic acid benzoyloxy-amide phenylamide. $^1$H NMR (DMSO-$d_6$) δ 11.85 (br s, 1H), 9.84 (s, 1H), 8.01 (d, J=8.0 Hz, 2H), 7.74 (t, J=7.8 Hz, 1H), 7.70-7.50 (m, 4H), 7.27 (t, J=7.4 Hz, 2H), 7.00 (t, J=6.8 Hz, 1H), 2.29 (t, J=7.4 Hz, 2H), 2.20 (t, J=7.4 Hz, 2H), 1.70-1.48 (m, 4H), 1.48-1.20 (m, 4H). MS (EI): cal'd (MH$^+$) 369.2, exp (MH$^+$) 369.2.

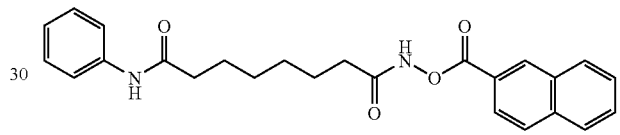

Octanedioic acid (naphthalene-2-carbonyloxy)-amide phenylamide. $^1$H NMR (DMSO-$d_6$) δ 11.85 (br s, 1H), 9.86 (s, 1H), 8.74 (s, 1H), 8.21-7.90 (m, 4H), 7.68 (t, J=7.4 Hz, 2H), 7.58 (d, J=7.6 Hz, 2H), 7.27 (t, J=7.8 Hz, 2H), 7.00 (t, J=7.6 Hz, 1H), 2.31 (t, J=7.4 Hz, 2H), 2.22 (t, J=7.4 Hz, 2H), 1.70-1.48 (m, 4H), 1.48-1.20 (m, 4H). MS (EI): cal'd (MH$^+$) 419.2, exp (MH$^+$) 419.1.

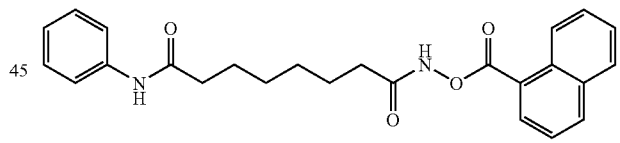

Octanedioic acid (naphthalene-1-carbonyloxy)-amide phenylamide. $^1$H NMR (DMSO-$d_6$) δ 12.00 (br s, 1H), 9.85 (s, 1H), 8.67 (d, J=7.4 Hz, 1H), 8.27 (d, J=8.4 Hz, 1H), 8.19 (d, J=7.0 Hz, 1H), 8.12-8.02 (m, 1H), 7.75-7.50 (m, 5H), 7.27 (t, J=7.6 Hz, 2H), 7.00 (t, J=7.6 Hz, 1H), 2.31 (t, J=7.4 Hz, 2H), 2.25 (t, J=7.4 Hz, 2H), 1.70-1.48 (m, 4H), 1.48-1.24 (m, 4H). MS (EI): cal'd (MH$^+$) 419.2, exp (MH$^+$) 419.1.

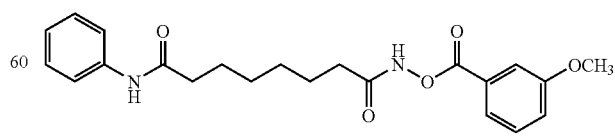

Octanedioic acid (3-methoxy-benzoyloxy)-amide phenylamide. $^1$H NMR (DMSO-$d_6$) δ 11.85 (br s, 1H), 9.84 (s, 1H), 7.65-7.45 (m, 5H), 7.35-7.20 (m, 3H), 7.00 (t, J=7.4 Hz, 1H), 3.83 (s, 3H), 2.30 (t, J=7.4 Hz, 2H), 2.19 (t, J=7.4 Hz, 2H), 1.70-1.45 (m, 4H), 1.45-1.25 (m, 4H). MS (EI): cal'd (MH+) 399.2, exp (MH+) 399.1.

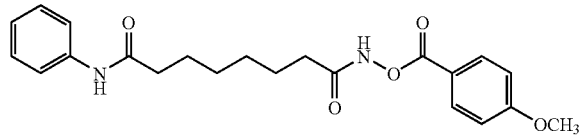

Octanedioic acid (4-methoxy-benzoyloxy)-amide phenylamide. ¹H NMR (DMSO-d₆) δ 11.85 (br s, 1H), 9.84 (s, 1H), 7.96 (d, J=8.8 Hz, 2H), 7.58 (d, J=7.8 Hz, 2H), 7.27 (t, J=8.0 Hz, 2H), 7.07 (d, J=8.8 Hz, 2H), 7.00 (t, J=7.2 Hz, 1H), 3.85 (s, 3H), 2.29 (t, J=7.4 Hz, 2H), 2.17 (t, J=7.4 Hz, 2H), 1.70-1.45 (m, 4H), 1.45-1.25 (m, 4H). MS (EI): cal'd (MH+) 399.2, exp (MH+) 399.2.

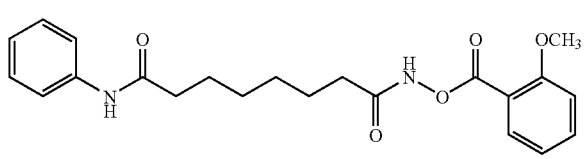

Octanedioic acid (2-methoxy-benzoyloxy)-amide phenylamide. ¹H NMR (DMSO-d₆) δ 11.85 (br s, 1H), 9.83 (s, 1H), 7.74 (dd, J1=7.6 Hz, J2=1.8 Hz, 1H), 7.65-7.50 (m, 3H), 7.27 (t, J=8.0 Hz, 2H), 7.23 (t, J=8.0 Hz, 1H), 7.06 (d, J=7.6 Hz, 1H), 7.00 (t, J=7.2 Hz, 1H), 3.84 (s, 3H), 2.29 (t, J=7.4 Hz, 2H), 2.17 (t, J=7.2 Hz, 2H), 1.70-1.45 (m, 4H), 1.45-1.25 (m, 4H). MS (EI): cal'd (MH+) 399.2, exp (MH+) 399.2.

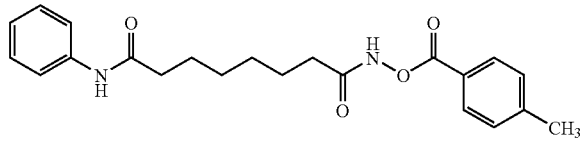

Octanedioic acid (4-methyl-benzoyloxy)-amide phenylamide. ¹H NMR (DMSO-d₆) δ 11.90 (br s, 1H), 9.84 (s, 1H), 7.90 (d, J=8.4 Hz, 2H), 7.58 (d, J=7.2 Hz, 2H), 7.38 (d, J=8.4 Hz, 2H), 7.27 (t, J=8.2 Hz, 2H), 7.00 (t, J=7.4 Hz, 1H), 2.40 (s, 3H), 2.30 (t, J=7.2 Hz, 2H), 2.17 (t, J=7.4 Hz, 2H), 1.70-1.45 (m, 4H), 1.45-1.25 (m, 4H). MS (EI): cal'd (MH+) 383.2, exp (MH+) 383.1.

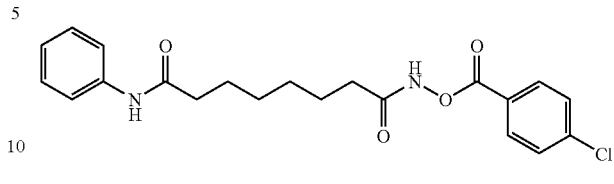

Octanedioic acid (4-chloro-benzoyloxy)-amide phenylamide. ¹H NMR (DMSO-d₆) δ 11.90 (br s, 1H), 9.83 (s, 1H), 8.02 (d, J=8.8 Hz, 2H), 7.66 (d, J=8.4 Hz, 2H), 7.57 (d, J=8.6 Hz, 2H), 7.27 (t, J=8.0 Hz, 2H), 7.00 (t, J=7.4 Hz, 1H), 2.29 (t, J=7.2 Hz, 2H), 2.19 (t, J=7.4 Hz, 2H), 1.70-1.45 (m, 4H), 1.45-1.25 (m, 4H). MS (EI): cal'd (MH+) 403.1, exp (MH+) 403.1.

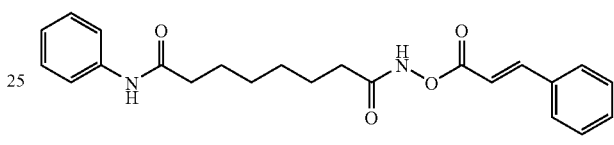

Octanedioic acid (3-phenyl-acryloyloxy)-amide phenylamide. ¹H NMR (DMSO-d₆) δ 11.85 (br s, 1H), 9.87 (s, 1H), 7.78 (d, J=16.0 Hz, 1H), 7.80-7.75 (m, 2H), 7.58 (d, J=7.6 Hz, 2H), 7.50-7.40 (m, 3H), 7.27 (t, J=8.0 Hz, 2H), 7.00 (t, J=7.4 Hz, 1H), 6.78 (d, J=16.0 Hz, 1H), 2.29 (t, J=7.4 Hz, 2H), 2.13 (t, J=7.4 Hz, 2H), 1.70-1.45 (m, 4H), 1.45-1.25 (m, 4H). MS (EI): cal'd (MH+) 395.2, exp (MH+) 395.2.

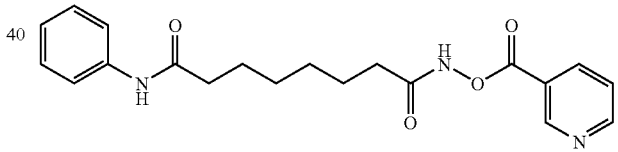

Octanedioic acid phenylamide(pyridine-3-carbonyloxy)-amide. ¹H NMR (DMSO-d₆) δ 11.92 (br s, 1H), 9.84 (s, 1H), 8.77 (d, J=4.8 Hz, 1H), 8.15-8.00 (m, 2H), 7.76-7.69 (m, 1H), 7.57 (d, J=7.8 Hz, 2H), 7.27 (t, J=7.8 Hz, 2H), 7.00 (t, J=7.8 Hz, 1H), 2.30 (t, J=7.4 Hz, 2H), 2.20 (t, J=7.4 Hz, 2H), 1.70-1.45 (m, 4H), 1.45-1.25 (m, 4H). MS (EI): cal'd (MH+) 370.2, exp (MH+) 370.2.

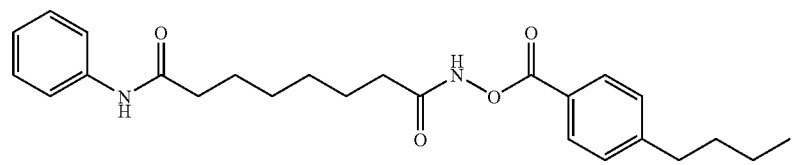

Octanedioic acid (4-butyl-benzoyloxy)-amide phenylamide. ¹H NMR (DMSO-d$_6$) δ 11.80 (br s, 1H), 9.84 (s, 1H), 7.92 (d, J=7.6 Hz, 1H), 7.58 (d, J=7.6 Hz, 2H), 7.40 (d, J=8.0 Hz, 2H), 7.27 (t, J=7.8 Hz, 2H), 7.00 (t, J=7.8 Hz, 1H), 2.68 (t, J=7.6 Hz, 2H), 2.30 (t, J=7.4 Hz, 2H), 2.18 (t, J=7.4 Hz, 2H), 1.70-1.45 (m, 6H), 1.45-1.25 (m, 6H), 0.89 (t, J=7.4 Hz, 3H). MS (EI): cal'd (MH⁺) 425.2, exp (MH⁺) 425.2.

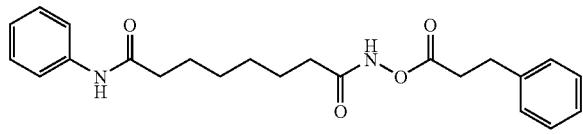

Octanedioic acid phenylamide(3-phenyl-propionyloxy)-amide. ¹H NMR (DMSO-d$_6$) δ 11.56 (br s, 1H), 9.83 (s, 1H), 7.57 (d, J=8.0 Hz, 2H), 7.35-7.15 (m, 7H), 7.00 (t, J=7.8 Hz, 1H), 2.88 (m, 2H), 2.78 (m, 2H), 2.28 (t, J=7.4 Hz, 2H), 2.10 (t, J=7.4 Hz, 2H), 1.70-1.45 (m, 4H), 1.45-1.25 (m, 4H). MS (EI): cal'd (MH⁺) 397.2, exp (MH⁺) 397.2.

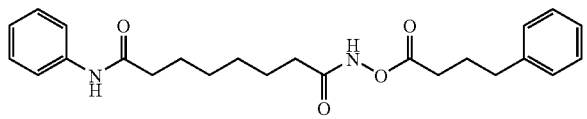

Octanedioic acid phenylamide(4-phenyl-butyryloxy)-amide. ¹H NMR (DMSO-d$_6$) δ 11.55 (br s, 1H), 9.82 (s, 1H), 7.57 (d, J=8.0 Hz, 2H), 7.35-7.15 (m, 7H), 7.00 (t, J=7.6 Hz, 1H), 2.64 (t, J=7.6 Hz, 2H), 2.42 (t, J=7.6 Hz, 2H), 2.28 (t, J=7.4 Hz, 2H), 2.11 (t, J=7.4 Hz, 2H), 1.85 (m, 2H), 1.70-1.45 (m, 4H), 1.45-1.25 (m, 4H). MS (EI): cal'd (MH⁺) 411.2, exp (MH⁺) 411.2.

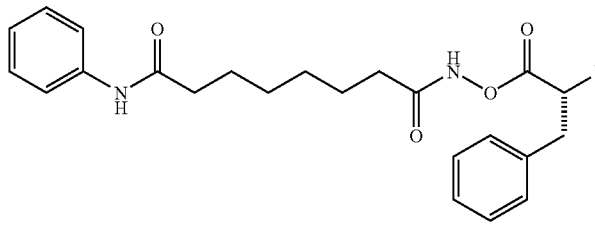

[1-Benzyl-2-oxo-2-(7-phenylcarbamoyl-heptanoylaminooxy)-ethyl]-carbamic acid benzyl ester. ¹H NMR (DMSO-d$_6$) δ 11.79 (br s, 1H), 9.84 (s, 1H), 8.00 (d, J=8.4 Hz, 1H), 7.57 (d, J=8.0 Hz, 2H), 7.40-7.10 (m, 12H), 7.00 (t, J=7.8 Hz, 1H), 4.97 (s, 2H), 4.43 (m, 1H), 3.30-2.70 (m, 2H), 2.28 (t, J=7.4 Hz, 2H), 2.13 (t, J=7.4 Hz, 2H), 1.70-1.45 (m, 4H), 1.45-1.25 (m, 4H). MS (EI): cal'd (MH⁺) 546.3, exp (MH⁺) 546.3.

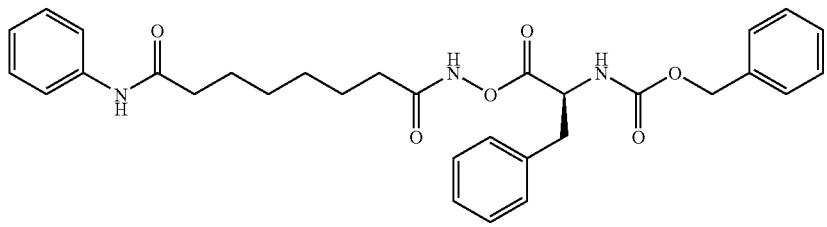

[1-Benzyl-2-oxo-2-(7-phenylcarbamoyl-heptanoylaminooxy)-ethyl]-carbamic acid benzyl ester. ¹H NMR (DMSO-d$_6$) δ 11.80 (br s, 1H), 9.85 (s, 1H), 7.97 (d, J=8.0 Hz, 1H), 7.58 (d, J=8.0 Hz, 2H), 7.40-7.10 (m, 12H), 7.00 (t, J=7.8 Hz, 1H), 4.97 (s, 2H), 4.42 (m, 1H), 3.25-2.80 (m, 2H), 2.28 (t, J=7.4 Hz, 2H), 2.11 (t, J=7.4 Hz, 2H), 1.70-1.45 (m, 4H), 1.45-1.25 (m, 4H). MS (EI): cal'd (MH⁺) 546.3, exp (MH⁺) 546.3.

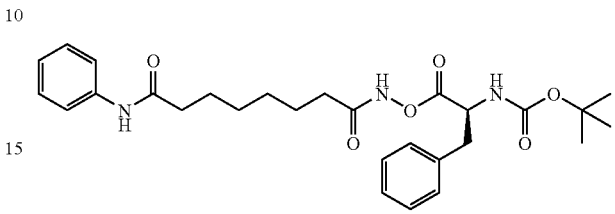

[1-Benzyl-2-oxo-2-(7-phenylcarbamoyl-heptanoylaminooxy)-ethyl]-carbamic acid tert-butyl ester. ¹H NMR (DMSO-d$_6$) δ 11.77 (br s, 1H), 9.83 (s, 1H), 7.57 (d, J=8.4 Hz, 2H), 7.47 (d, J=8.4 Hz, 1H), 7.35-7.15 (m, 7H), 7.00 (t, J=7.4 Hz, 1H), 4.31 (m, 1H), 3.20-2.80 (m, 2H), 2.28 (t, J=7.4 Hz, 2H), 2.12 (t, J=7.4 Hz, 2H), 1.70-1.45 (m, 4H), 1.45-1.25 (m, 4H), 1.30 (s, 9H). MS (EI): cal'd (MH⁺) 512.3, exp (MH⁺) 512.3.

Example 2

HDAC Inhibition by SAHA Prodrugs

HDAC1-Flag Assay:

Novel compounds were tested for their ability to inhibit histone deacetylase, subtype 1 (HDAC1) using an in vitro deacetylation assay. The enzyme source for this assay was an epitope-tagged human HDAC1 complex immuno-purified from stably expressing mammalian cells. The substrate consisted of a commercial product containing an acetylated lysine side chain (BIOMOL Research Laboratories, Inc., Plymouth Meeting, Pa.). Upon deacetylation of the substrate by incubation with the purified HDAC1 complex, a fluorophore is produced that is directly proportional to the level of deacetylation. Using a substrate concentration at the Km for

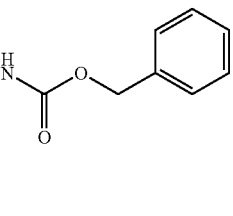

the enzyme preparation, the deacetylation assay was performed in the presence of increasing concentrations of novel compounds to semi-quantitatively determine the concentration of compound required for 50% inhibition (IC$_{50}$) of the deacetylation reaction.

Results:

Table 1 below shows the chemical structures and HDAC enzymatic assay results for a selection of novel SAHA prodrugs designed and synthesized in accordance with the present invention.

TABLE 1

| No. | Structure | MW | HDAC1 IC50 Ave (nM) | HDAC1 % INH 10 μM | HDAC1 % INH 100 μM |
|---|---|---|---|---|---|
| SAHA | 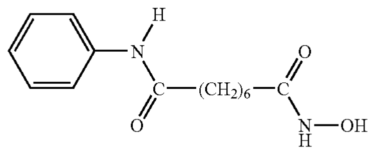 | 264 | 45 ± 17.1 (N = 68) | | |
| I | 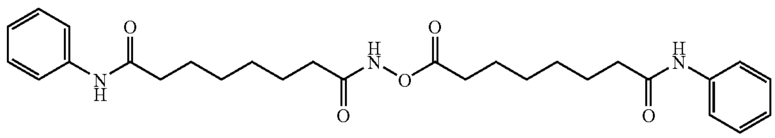 | 495.62 | 51850 (N = 1) | 45 (N = 1) | 79 (N = 1) |
| II | 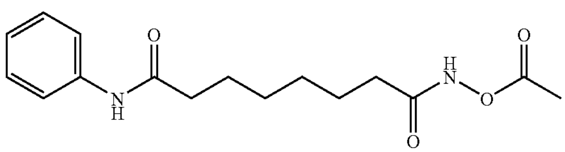 | 306.36 | | −17 (N = 1) | 2 (N = 1) |
| III | 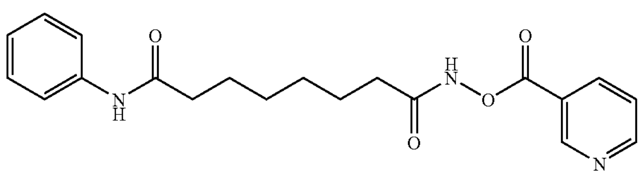 | 369.42 | 582.5 ± 311.8 (N = 2) | 87 (N = 1) | 97 (N = 1) |
| IV | 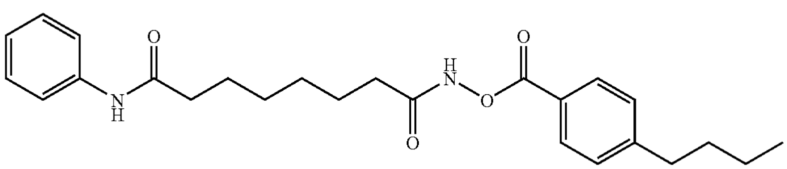 | 424.54 | | 10 (N = 1) | 50 (N = 1) |
| V | 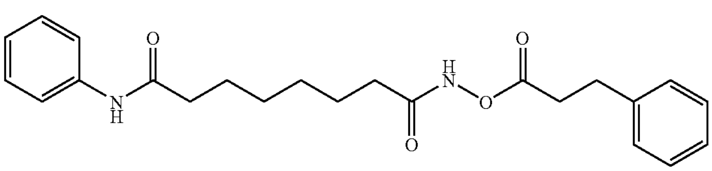 | 396.49 | 1676 ± 1202 (N = 2) | 64 (N = 1) | 90 (N = 1) |
| VI | 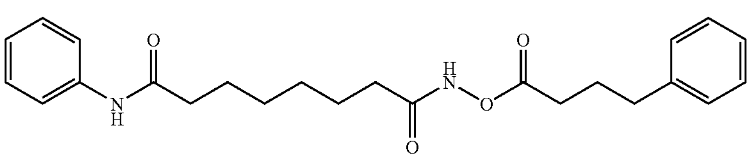 | 410.51 | | 27 (N = 1) | 62 |
| VII | 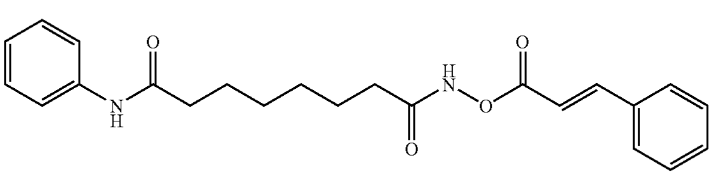 | 394.47 | | 26 (N = 1) | 45 (N = 1) |

TABLE 1-continued

| No. | Structure | MW | HDAC1 IC50 Ave (nM) | HDAC1 % INH 10 μM | HDAC1 % INH 100 μM |
|---|---|---|---|---|---|
| VIII | 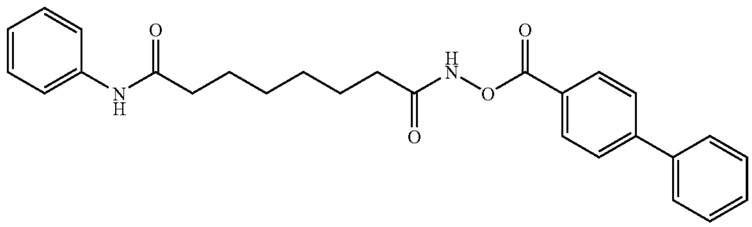 | 444.53 | | 94 (N = 1) | 99 (N = 1) |
| IX | 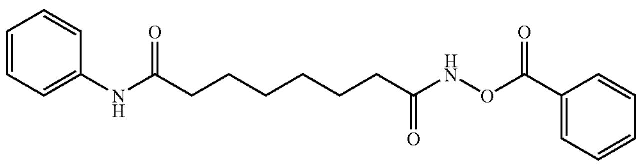 | 368.43 | | 20 (N = 1) | 60 (N = 1) |
| X | 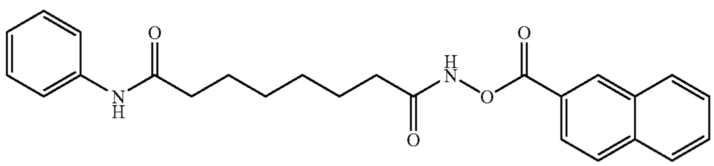 | 418.49 | | 9 (N = 1) | 22 (N = 1) |
| XI | 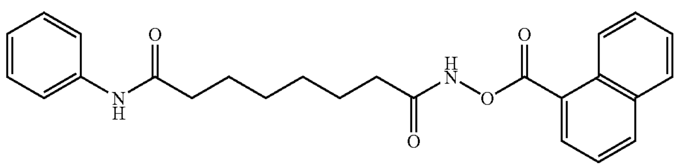 | 418.49 | | 5 (N = 1) | 5 (N = 1) |
| XII | 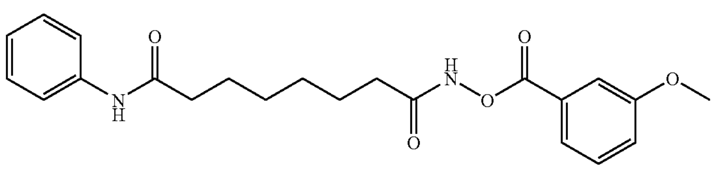 | 398.46 | | 20 | 43 (N = 1) |
| XIII | 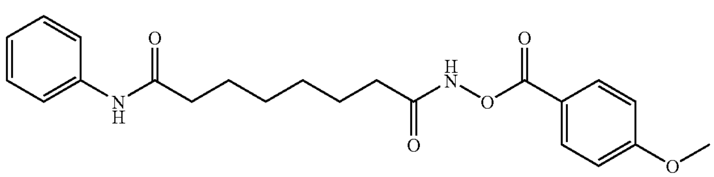 | 398.46 | | 21 (N = 1) | 65 (N = 1) |
| XIV | 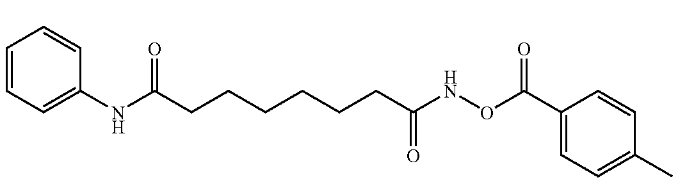 | 382.46 | | 38 (N = 1) | 74 (N = 1) |
| XV | 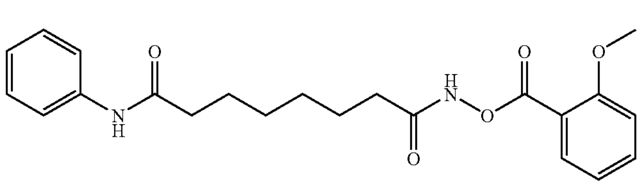 | 398.46 | | 23 (N = 1) | 48 (N = 1) |

TABLE 1-continued

| No. | Structure | MW | HDAC1 IC50 Ave (nM) | HDAC1 % INH 10 μM | HDAC1 % INH 100 μM |
|---|---|---|---|---|---|
| XVI | [structure] | 402.88 | | 24 (N = 1) | 36 (N = 1) |
| XVII | [structure] | 545.63 | | 94 (N = 1) | 99 (N = 1) |
| XVIII | [structure] | 545.63 | | 78 (N = 1) | 93 (N = 1) |
| XIX | [structure] | 511.62 | | 87 (N = 1) | 96 (N = 1) |

Example 3

HDAC Inhibition in Cell Lines

MTS Assay

The novel compounds of the present invention were tested for their ability to inhibit proliferation of the murine erythroleukemia cell line SC9. The MTS assay, also referred to as the Cell Titer 96 Aqueous One Solution Cell Proliferation Assay, is a colorimetric method for determining the number of viable cells in proliferation, cytotoxicity, or chemosensitivity assays. The MTS reagent contains a novel tetrazolium compound [3-(4,5-dimethylthiazol-2-yl)-5-(3-carboxymethoxyphenyl)-2-(4-sulfophenyl)-2H-tetrazolium, inner salt] and electron coupling reagent (phenazine ethosulfate; PES). Murine erythroleukemia cells (SC-9) were incubated with vehicle or increasing concentrations of compound for 48 hours. Cell proliferation was quantitated by adding a small amount of the MTS reagent directly to culture wells, incubating for 1-4 hours and then recording the absorbance at 490 nM with a 96-well plate reader. The quantity of formazan product, as measured by 490 nM absorbance, is directly proportional to the number of living cells in culture.

Results

The results of the SC9-cell based MTS assay from a select group of novel compounds are summarized in Table 2 below:

TABLE 2

| No. | Structure | MTS Assay |
|---|---|---|
| SAHA | [structure] | 515 ± 171 nM (N = 59) |

TABLE 2-continued

| No. | Structure | MTS Assay |
|---|---|---|
| I | 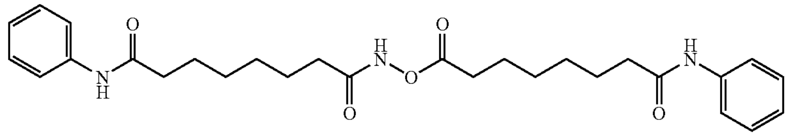 | 785 ± 4.9 (N = 2) |
| II | 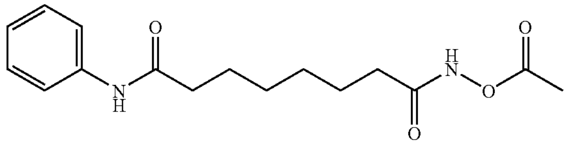 | 246 ± 78.4 (N = 2) |
| III | 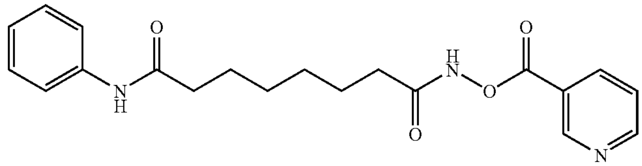 | 252 ± 56.5 (N = 2) |
| IV | 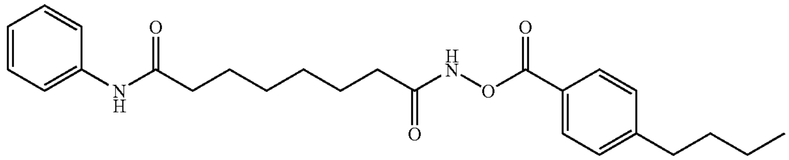 | 1764 (N = 1) |
| V | 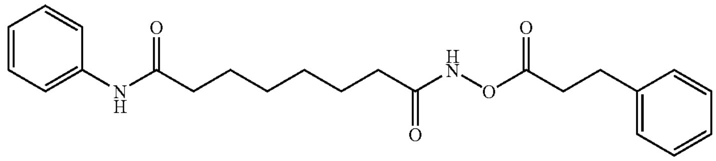 | 491 ± 327.2 (N = 3) |
| VI | 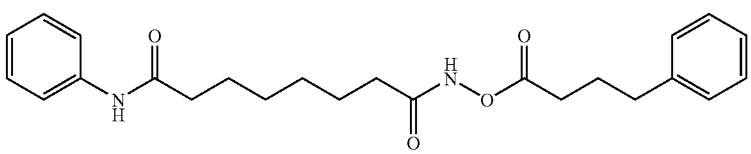 | 1544 (N = 1) |
| VII | 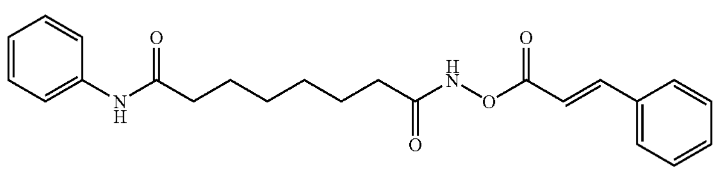 | 648 (N = 1) |
| VIII | 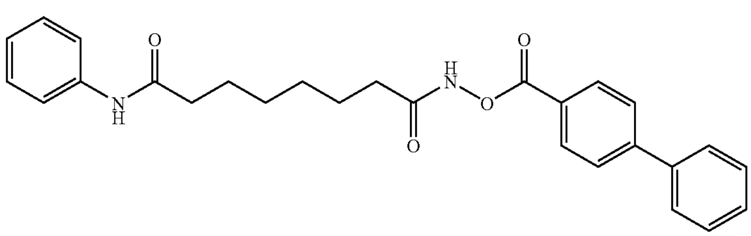 | 1376 (N = 1) |
| IX | 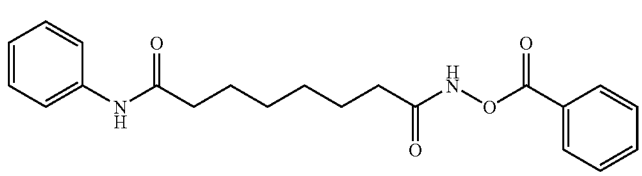 | 1204 (N = 1) |

TABLE 2-continued

| No. | Structure | MTS Assay |
|---|---|---|
| X | 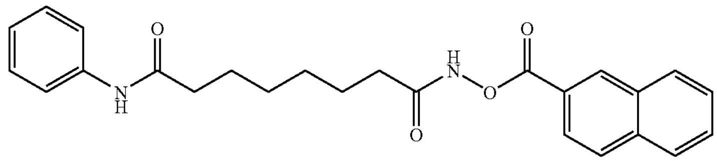 | 1787 (N = 1) |
| XI | 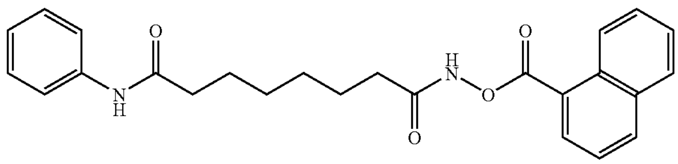 | 5218 (N = 1) |
| XII | 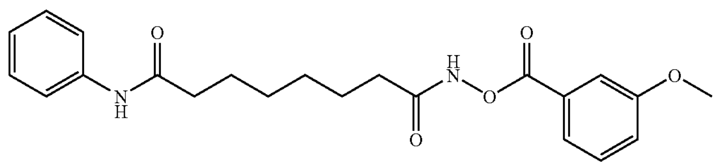 | 494 (N = 1) |
| XIII | 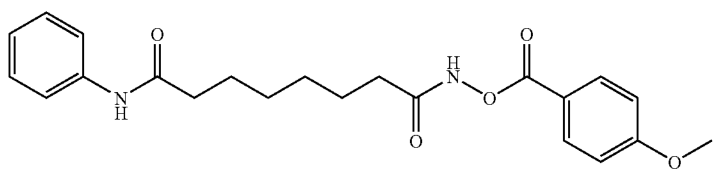 | 748 (N = 1) |
| XIV | 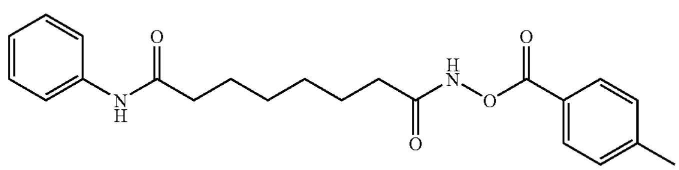 | 862 (N = 1) |
| XV | 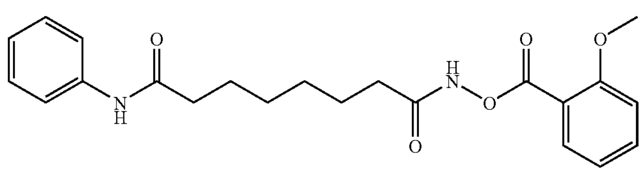 | 592 (N = 1) |
| XVI | 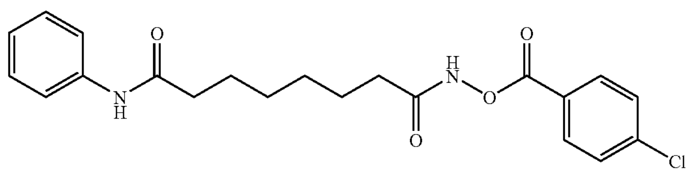 | 434 (N = 1) |
| XVII | 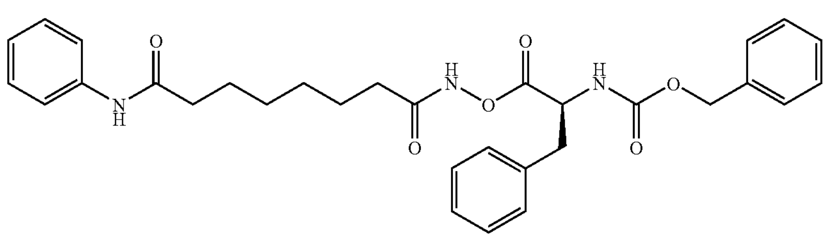 | 753 (N = 1) |

TABLE 2-continued

| No. | Structure | MTS Assay |
|---|---|---|
| XVIII | (structure) | 443 (N = 1) |
| XIX | (structure) | 446 (N = 1) |

The data shows that the compounds of the invention show little activity as HDAC inhibitors in an in-vitro HDAC inhibition assay, and that these compounds are much less potent at inhibiting HDAC-1 as compared to the parent molecule SAHA (Table 1). However, in cell lines, these compounds are potent inhibitors of proliferation of the murine erythroleukemia cell line SC9, in around the same order of magnitude of SAHA (Table 2).

Without wishing to be bound to any particular, one possible mechanism by which the compounds of the present invention are acting is that these compounds are converted inside the cell to the free hydroxamic acid, thus providing an active form of the compound, which is able to inhibit cellular proliferation. This data is consistent with the ability of these compounds to act as SAHA prodrugs.

While this invention has been particularly shown and described with references to preferred embodiments thereof, it will be understood by those skilled in the art that various changes in form and details may be made therein without departing from the meaning of the invention described. Rather, the scope of the invention is defined by the claims that follow.

What is claimed is:

1. A compound represented by the structure of formula 1:

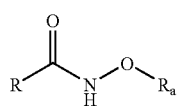

(1)

wherein R is a residue of a hydroxamic acid derivative histone deacetylase inhibitor; and $R_a$ is represented by the structure:

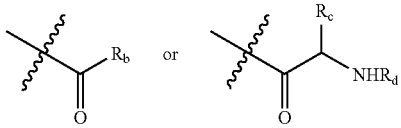

wherein $R_b$ is a hydrogen or an unsubstituted or substituted ethyl, isopropyl, butyl, isobutyl, sec-butyl, t-butyl, alkynyl, naphthyl, cycloalkyl, heterocyclyl, heteroaryl, alkylaryl, alkylcycloalkyl, alkylheterocyclyl, alkylheteroaryl or an amino acid residue; $R_c$ is a hydrogen or an unsubstituted or substituted alkyl, alkenyl, alkynyl, aryl, cycloalkyl, heterocyclyl, heteroaryl, alkylaryl, alkylcycloalkyl, alkylheterocyclyl, alkylheteroaryl or an amino acid residue and $R_d$ is hydrogen or an amino protecting group;

or a pharmaceutically acceptable salt thereof.

2. The compound according to claim 1, wherein $R_b$ is a hydrogen, ethyl, isopropyl, butyl, isobutyl, sec-butyl, t-butyl, benzyl, alkylphenyl, napthyl or pyridyl;

$R_c$ is a hydrogen, methyl, ethyl, isopropyl, butyl, isobutyl, sec-butyl, t-butyl, phenyl, benzyl, alkylphenyl, napthyl or pyridyl.

3. The compound according to claim 1, wherein $R_a$ is selected from the group consisting of:

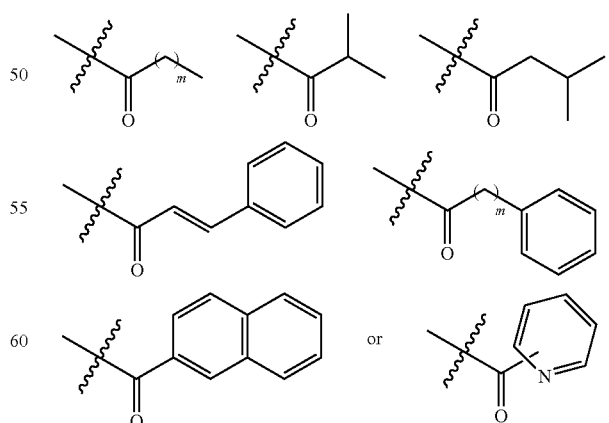

and wherein m is an integer of 1 to 10.

4. A compound represented by the structure:

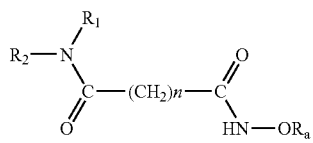
(2)

wherein each of $R_1$ and $R_2$ are independently the same as or different from each other and are a hydrogen atom, a hydroxyl group, a substituted or unsubstituted, branched or unbranched alkyl, alkenyl, cycloalkyl, aryl, heterocyclyl, heteroaryl, alkylcycloalkyl, alkylaryl, alkylheterocyclyl, alkylheteroaryl, arylalkyloxy, aryloxy, or pyridine group, or $R_1$ and $R_2$ are bonded together to form a nitrogen containing heterocyclic ring optionally containing one or more additional heteroatoms, and n is an integer of 4 to 8;

$R_a$ is represented by the structure:

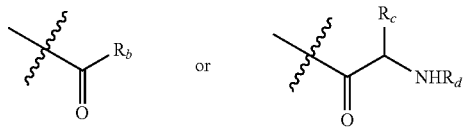

wherein $R_b$ and $R_c$ are independently of each other a hydrogen or an unsubstituted or substituted alkyl, alkenyl, alkynyl, aryl, cycloalkyl, heterocyclyl, heteroaryl, alkylaryl, alkylcycloalkyl, alkylheterocyclyl, alkylheteroaryl or an amino acid residue; and $R_d$ is hydrogen or an amino protecting group.

5. The compound according to claim 4, represented by the structure:

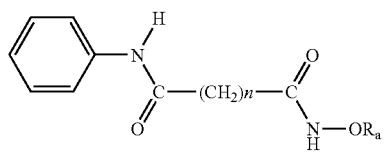
(3)

wherein n is an integer of 4 to 8.

6. The compound according to claim 5, represented by the structure:

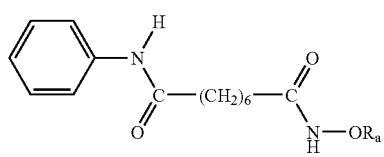
(4)

$R_a$ is selected from the group consisting of:

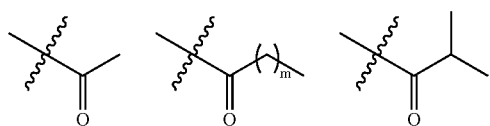

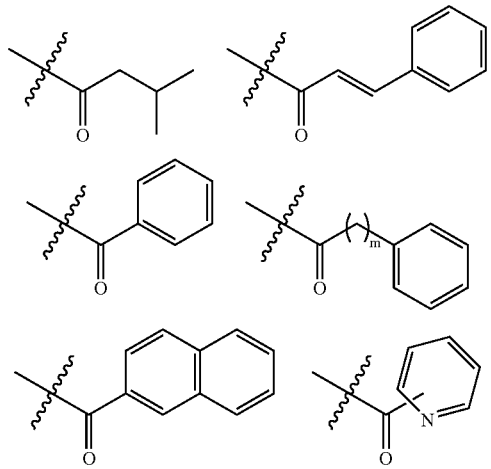

and wherein m is an integer of 1 to 10.

7. The compound according to claim 1, represented by the structure:

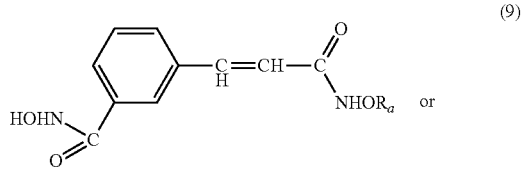
(9)

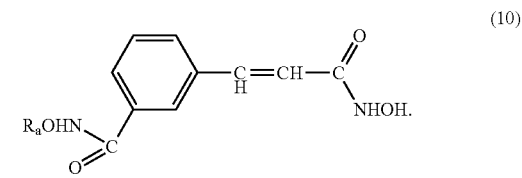
(10)

8. The compound according to claim 1, represented by the structure:

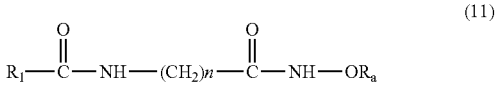
(11)

wherein $R_1$ is a substituted or unsubstituted phenyl, piperidino, thiazolyl, 2-pyridinyl, 3-pyridinyl or 4-pyridinyl and n is an integer of 4 to 8.

9. The compound according to claim 1, represented by the structure:

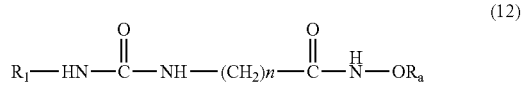
(12)

wherein $R_1$ is a substituted or unsubstituted phenyl, piperidino, thiazolyl, 2-pyridinyl, 3-pyridinyl or 4-pyridinyl and n is an integer of 4 to 8.

10. The compound according to claim 1, represented by the structure:

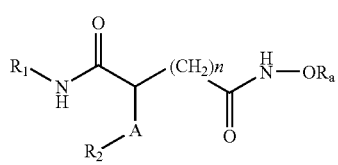

(13)

wherein A is an amide moiety, $R_1$ and $R_2$ are each selected from substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; and n is an integer of 3 to 10.

11. The compound according to claim 10, represented by the structure:

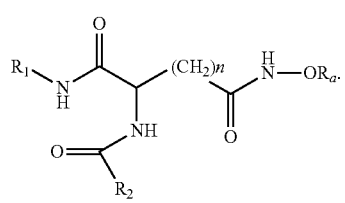

(13a)

12. The compound according to claim 10, represented by the structure:

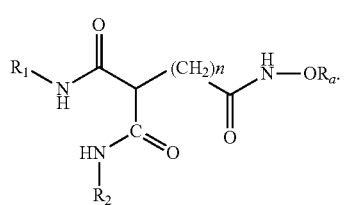

(13b)

13. The compound according to claim 1, represented by the structure:

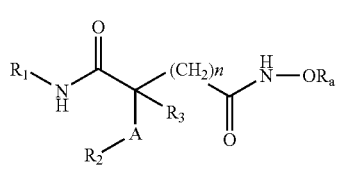

(14)

wherein A is an amide moiety, $R_1$ and $R_2$ are each selected from substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; $R_3$ is hydrogen, a halogen, a phenyl or a cycloalkyl moiety and n is an integer of 3 to 10.

14. The compound according to claim 13, represented by the structure:

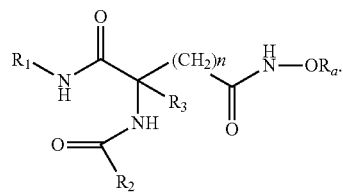

(14a)

15. The compound according to claim 13, represented by the structure:

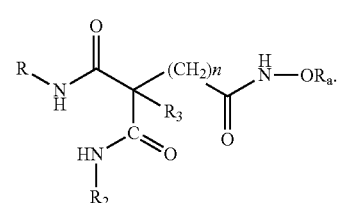

(14b)

wherein n is an integer from about 3 to 10.

16. The compound according to claim 1, represented by the structure:

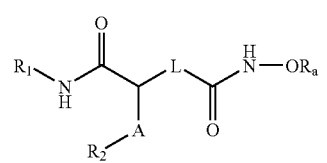

(15)

wherein L is a linker selected from the group consisting of an amide moiety, O—, —S—, —NH—, NR, —CH$_2$—, —(CH$_2$)$_p$—, —(CH═CH)—, phenylene, cycloalkylene, or any combination thereof wherein R is a substituted or unsubstituted $C_1$-$C_5$ alkyl; and wherein each of $R_1$ and $R_2$ are independently a substituted or unsubstituted aryl, arylalkyl, naphthyl, cycloalkyl, cycloalkylamino, pyridineamino, piperidino, 9-purine-6-amino, thiazoleamino, hydroxyl, branched or unbranched alkyl, alkenyl, alkyloxy, aryloxy, arylalkyloxy, pyridyl, quinolinyl or isoquinolinyl; p is an integer of 0 to 10.

17. The compound according to claim 16, represented by the structure:

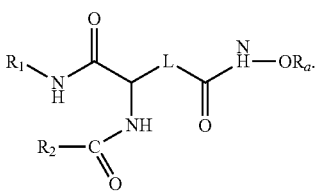

(15b)

18. The compound according to claim 1, represented by the structure:

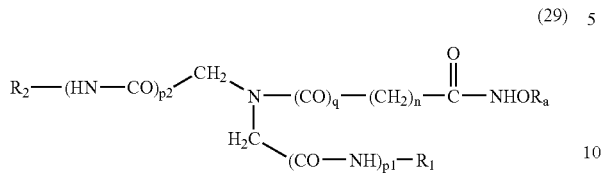
(29)

wherein n is 2, 3, 4, 5, 6, 7 or 8;

q is 0 or 1;

$p_1$ and $p_2$ are independently of each other 0 or 1;

$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or when $p_1$ and $p_2$ are both 0, $R_1$ and $R_2$ together with the —$CH_2$—N—$CH_2$— group to which they are attached can also represent a nitrogen-containing heterocyclic ring; or when at least one of $p_1$ or $p_2$ is not 0, $R_1$ or $R_2$ or both can also represent hydrogen or alkyl.

19. The compound according to claim 1, represented by the structure:

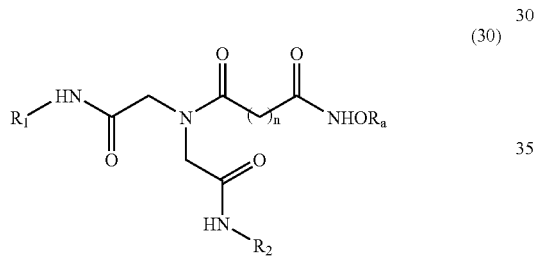
(30)

wherein n is 2, 3, 4, 5, 6, 7 or 8;

$R_1$ and $R_2$ are independently of each other a hydrogen or an unsubstituted or substituted alkyl, aryl, heteroaryl, cycloalkyl, heterocyclyl, alkylaryl, alkylheteroaryl, alkylcycloalkyl or alkylheterocyclyl.

20. The compound according to claim 1, represented by the structure:

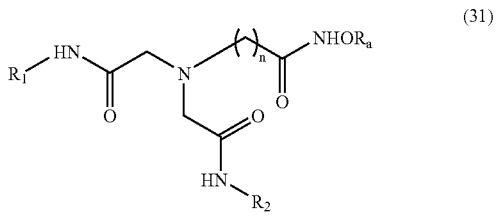
(31)

wherein n is 2, 3, 4, 5, 6, 7 or 8;

$R_1$ and $R_2$ are independently of each other a hydrogen or an unsubstituted or substituted alkyl, aryl, heteroaryl, cycloalkyl, heterocyclyl, alkylaryl, alkylheteroaryl, alkylcycloalkyl or alkylheterocyclyl.

21. The compound according to claim 1, represented by the structure:

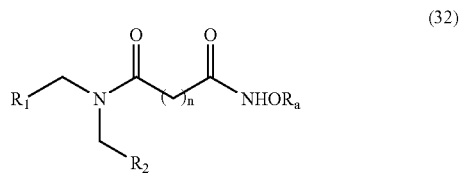
(32)

wherein n is 2, 3, 4, 5, 6, 7 or 8;

$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or $R_1$ and $R_2$ together with the —$CH_2$—N—$CH_2$— group to which they are attached can also represent a nitrogen-containing heterocyclic ring.

22. The compound according to claim 1, represented by the structure:

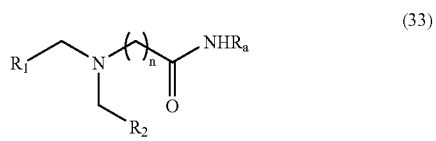
(33)

wherein n is 2, 3, 4, 5, 6, 7 or 8;

$R_1$ and $R_2$ are independently of each other an unsubstituted or substituted aryl, heteroaryl, cycloalkyl, heterocyclyl, alkylaryl, alkylheteroaryl, alkylcycloalkyl or alkylheterocyclyl; or $R_1$ and $R_2$ together with the —$CH_2$—N—$CH_2$— group to which they are attached can also represent a nitrogen-containing heterocyclic ring.

23. The compound according to claim 1, represented by the structure:

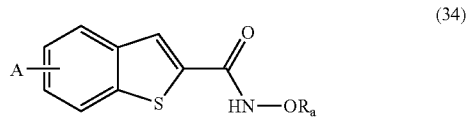
(34)

wherein A is alkyl, aryl or a group selected from

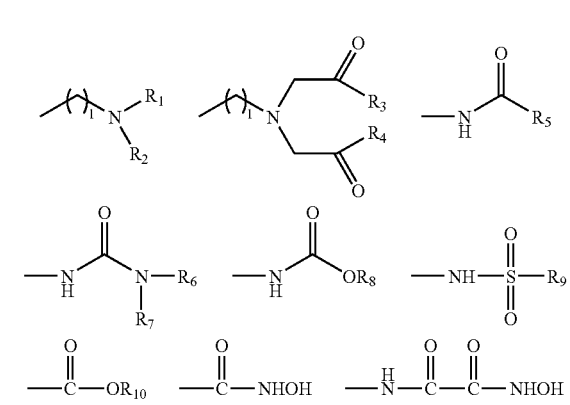

-continued

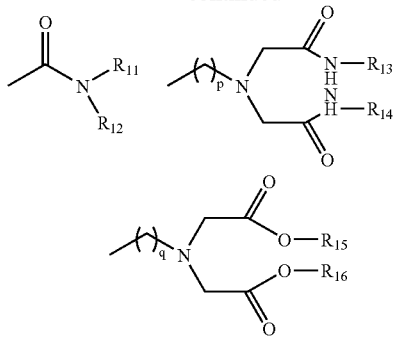

wherein $R_1$-$R_{16}$ are independently of each other a hydrogen or an unsubstituted or substituted alkyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring; and l, p and q are independently of each other 0, 1 or 2.

24. The compound according to claim 1, represented by the structure:

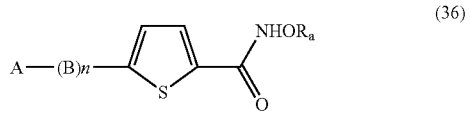

wherein
A is alkyl, aryl or a group selected from:

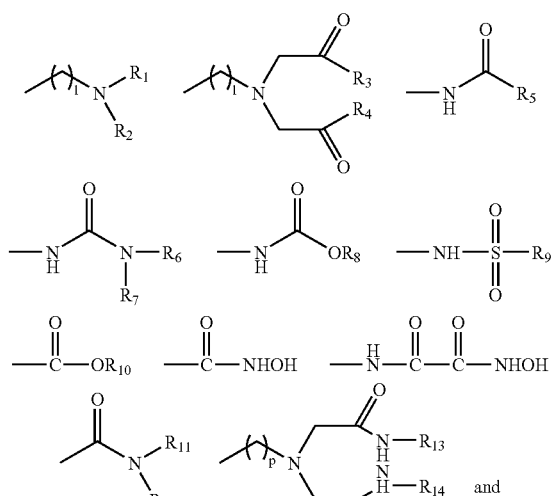

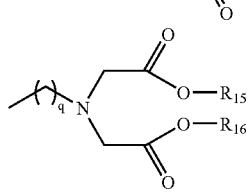

wherein $R_1$-$R_{16}$ are independently of each other a hydrogen or an unsubstituted or substituted alkyl, aryl, cycloalkyl, heterocyclyl, alkylaryl, alkylcycloalkyl or alkylheterocyclyl; or one or more of $R_1$ and $R_2$, $R_6$ and $R_7$, and $R_{11}$ and $R_{12}$, together with the nitrogen atom to which they are attached, form a nitrogen-containing heterocyclic ring;

B is

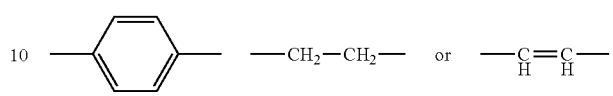

n is 0 or 1; and
l, p and q are independently of each other 0, 1 or 2.

25. A pharmaceutical composition comprising the compound of claim 1 or a pharmaceutically acceptable salt thereof, and a pharmaceutically acceptable carrier.

26. The compound of claim 4 selected from the group consisting of:
Octanedioic acid phenylamide (7-phenylcarbamoyl-heptanoyloxy)-amide;
Octanedioic acid acetoxy-amide phenylamide;
Octanedioic acid (biphenyl-4-carbonyloxy)-amide phenylamide;
Octanedioic acid benzoyloxy-amide phenylamide;
Octanedioic acid (naphthalene-2-carbonyloxy)-amide phenylamide;
Octanedioic acid (naphthalene-1-carbonyloxy)-amide phenylamide;
Octanedioic acid (3-methoxy-benzoyloxy)-amide phenylamide;
Octanedioic acid (4-methoxy-benzoyloxy)-amide phenylamide;
Octanedioic acid (2-methoxy-benzoyloxy)-amide phenylamide;
Octanedioic acid (4-methyl-benzoyloxy)-amide phenylamide;
Octanedioic acid (4-chloro-benzoyloxy)-amide phenylamide;
Octanedioic acid (3-phenyl-acryloyloxy)-amide phenylamide;
Octanedioic acid phenylamide (pyridine-3-carbonyloxy)-amide;
Octanedioic acid (4-butyl-benzoyloxy)-amide phenylamide;
Octanedioic acid phenylamide (3-phenyl-propionyloxy)-amide;
Octanedioic acid phenylamide (4-phenyl-butyryloxy)-amide;
[1-Benzyl-2-oxo-2-(7-phenylcarbamoyl-heptanoylaminooxy)-ethyl]-carbamic acid benzyl ester; and
[1-Benzyl-2-oxo-2-(7-phenylcarbamoyl-heptanoylaminooxy)-ethyl]-carbamic acid tert-butyl ester;
Or a stereoisomer thereof;
Or a pharmaceutically acceptable salt thereof;
Or a pharmaceutically acceptable salt of the stereoisomer thereof.

27. The compound of claim 4 that is

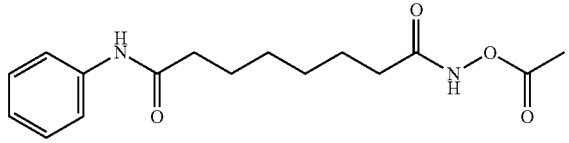

or a pharmaceutically acceptable salt thereof.

28. The compound of claim 4 that is

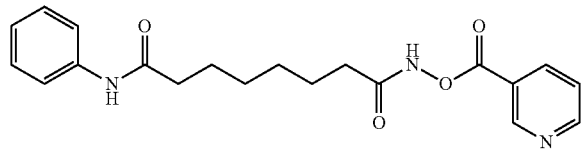

or a pharmaceutically acceptable salt thereof.

29. A pharmaceutical composition comprising the compound of claim 26 and a pharmaceutically acceptable carrier.

30. The compound according to claim 5, wherein $R_b$ is a hydrogen, methyl, ethyl, isopropyl, butyl, isobutyl, sec-butyl, t-butyl, phenyl, benzyl, alkylphenyl, napthyl or pyridyl;

$R_c$ is a hydrogen, methyl, ethyl, isopropyl, butyl, isobutyl, sec-butyl, t-butyl, phenyl, benzyl, alkylphenyl, napthyl or pyridyl.

* * * * *